(12) United States Patent
Doll et al.

(10) Patent No.: US 9,192,762 B2
(45) Date of Patent: Nov. 24, 2015

(54) THERAPEUTIC MICRO-CURRENT DELIVERY DEVICES AND METHODS THEREOF

(75) Inventors: Alexander F. Doll, Kronberg (DE); Julie Myers Grender, Cincinnati, OH (US); Phyllis D. Hoke, Loveland, OH (US); Malgorzata Klukowska, Mason, OH (US); David Salloum, West Chester, OH (US); Donald James White, Jr., Fairfield, OH (US); Soujanya Chinnapareddy, Vijayawada (IN)

(73) Assignee: Braun GmbH, Kronberg (DE)

( * ) Notice: Subject to any disclaimer, the term of this patent is extended or adjusted under 35 U.S.C. 154(b) by 38 days.

(21) Appl. No.: 13/615,667

(22) Filed: Sep. 14, 2012

(65) Prior Publication Data

US 2013/0072851 A1    Mar. 21, 2013

Related U.S. Application Data

(60) Provisional application No. 61/536,678, filed on Sep. 20, 2011.

(51) Int. Cl.
*A61N 1/32* (2006.01)
*A46B 15/00* (2006.01)
(Continued)

(52) U.S. Cl.
CPC ............. *A61N 1/322* (2013.01); *A46B 15/00* (2013.01); *A46B 15/0008* (2013.01);
(Continued)

(58) Field of Classification Search
CPC ....... A61N 1/0428; A61N 1/30; A61N 1/306; A61N 1/322; A61N 1/325; A61N 1/18; A61N 1/26; A61N 1/32; A46B 15/0016; A46B 15/0022; A46B 15/0024; A46B 15/0004; A46B 15/0008; A46B 2200/1066; A61C 17/22; A61C 17/221; A61C 17/222
USPC .............. 604/20, 21, 22, 501; 433/29; 607/72
See application file for complete search history.

(56) References Cited

U.S. PATENT DOCUMENTS

| 3,520,297 A | 7/1970 | Bechtold |
| 4,691,718 A | 9/1987 | Sakuma et al. |

(Continued)

FOREIGN PATENT DOCUMENTS

| CN | 000002678597 Y | 2/2005 |
| CN | 000101340856 A | 1/2009 |

(Continued)

OTHER PUBLICATIONS

Huysmans et al, "Impedance Spectroscopy of Teeth with and without Approximal Caries Lesions—an in vitro Study", J. Dent. Res 75(11): 1871-1878, Nov. 1996.

(Continued)

*Primary Examiner* — Kami A Bosworth
(74) *Attorney, Agent, or Firm* — Alexandra S. Anoff

(57) ABSTRACT

A therapeutic micro-current delivery device includes a first electrode in electrical contact with a user at a first user location, a second electrode in electrical contact with the user at a second user location, a power source operable to provide a first voltage potential at the first electrode and a second voltage potential at the second electrode, and a micro-current control circuit in electrical communication with the first electrode, second electrode and power source. Electrical contact of the first electrode at the first user location and electrical contact of the second electrode at the second user location completes an electrical circuit. The micro-current control circuit generates a micro-current $I_{ramped}$ through a user between the first location and the second location that increases from a start current $I_{start}$ to an end current $I_{end}$ over a rise time $t_{rise}$. Oral care devices and micro-current control methods are also disclosed.

23 Claims, 10 Drawing Sheets

(51) Int. Cl.
*A61N 1/26* (2006.01)
*A61N 1/30* (2006.01)
*A61C 17/22* (2006.01)
*A61C 19/04* (2006.01)
*A61N 5/06* (2006.01)

(52) U.S. Cl.
CPC ........ *A46B 15/0022* (2013.01); *A46B 15/0024* (2013.01); *A61C 17/22* (2013.01); *A61C 17/221* (2013.01); *A61C 17/222* (2013.01); *A61C 19/04* (2013.01); *A61N 1/26* (2013.01); *A61N 1/306* (2013.01); *A61N 1/32* (2013.01); *A61N 5/0601* (2013.01); *A46B 2200/1066* (2013.01)

(56) References Cited

U.S. PATENT DOCUMENTS

| | | | |
|---|---|---|---|
| 4,969,868 | A | 11/1990 | Wang |
| 5,280,429 | A | 1/1994 | Withers |
| 5,372,501 | A | 12/1994 | Shalvi |
| 5,706,542 | A | 1/1998 | Okada |
| 5,935,156 | A * | 8/1999 | Chandler et al. .............. 607/66 |
| 6,432,387 | B1 | 8/2002 | Kaizuka |
| 6,743,015 | B2 | 6/2004 | Magnani |
| 6,918,300 | B2 | 7/2005 | Grez et al. |
| 6,952,855 | B2 | 10/2005 | Lev et al. |
| 6,952,856 | B2 | 10/2005 | Kaizuka |
| 7,270,878 | B2 | 9/2007 | Kaizuka |
| 7,466,040 | B2 | 12/2008 | Bruwer |
| 7,624,467 | B2 | 12/2009 | Hilscher et al. |
| 7,775,795 | B2 | 8/2010 | Khawaled et al. |
| 7,886,398 | B2 | 2/2011 | Morita et al. |
| 7,975,341 | B2 | 7/2011 | Cai et al. |
| 8,145,325 | B2 | 3/2012 | Taniguchi et al. |
| 8,858,580 | B2 | 10/2014 | Schaefer et al. |
| 2001/0009983 | A1* | 7/2001 | Walter et al. ................. 604/20 |
| 2003/0163170 | A1 | 8/2003 | Faisandier |
| 2004/0193235 | A1 | 9/2004 | Altshuler et al. |
| 2005/0266373 | A1 | 12/2005 | Lin |
| 2006/0270942 | A1 | 11/2006 | McAdams |
| 2007/0232983 | A1 | 10/2007 | Smith |
| 2007/0259310 | A1 | 11/2007 | Goodson et al. |
| 2008/0060148 | A1 | 3/2008 | Pinyayev et al. |
| 2008/0083074 | A1 | 4/2008 | Taniguchi et al. |
| 2009/0264792 | A1 | 10/2009 | Mazar |
| 2010/0204637 | A1* | 8/2010 | Imran .............................. 604/20 |
| 2010/0281636 | A1 | 11/2010 | Ortins |
| 2011/0080122 | A1 | 4/2011 | Klemm et al. |
| 2013/0071805 | A1 | 3/2013 | Doll et al. |
| 2013/0071806 | A1 | 3/2013 | Doll et al. |
| 2013/0071807 | A1 | 3/2013 | Doll et al. |
| 2013/0072851 | A1 | 3/2013 | Doll et al. |

FOREIGN PATENT DOCUMENTS

| | | |
|---|---|---|
| DE | 4012413 A1 | 10/1991 |
| DE | 196 05 845 A1 | 8/1997 |
| DE | 101 59 395 A1 | 6/2003 |
| DE | 10244575 B3 | 5/2004 |
| DE | 10 2004 022 663 A1 | 12/2005 |
| DE | 10 2004 029 684 | 12/2005 |
| DE | 10 2005 007 919 A1 | 8/2006 |
| EP | 1935371 A1 | 6/2008 |
| EP | 1980375 A1 | 10/2008 |
| EP | 2 522 303 A1 | 11/2012 |
| GB | 2030855 A | 4/1980 |
| GB | 2317555 A | 4/1998 |
| GB | 2414658 A | 12/2005 |
| JP | 61-048356 A | 3/1986 |
| JP | 63-300710 A | 12/1988 |
| JP | 21-59208 A | 6/1990 |
| JP | 22-24615 A | 9/1990 |
| JP | 22-77407 A | 11/1990 |
| JP | 22-83311 A | 11/1990 |
| JP | 23-09908 A | 12/1990 |
| JP | 42-15706 A | 8/1992 |
| JP | 53-05010 A | 11/1993 |
| JP | 61-81996 A | 7/1994 |
| JP | 80-80219 A | 3/1996 |
| JP | 08-275961 A | 10/1996 |
| JP | 90-00351 A | 1/1997 |
| JP | 90-65931 A | 3/1997 |
| JP | 91-40453 A | 6/1997 |
| JP | 91-91936 A | 7/1997 |
| JP | 92-66818 A | 10/1997 |
| JP | 10-042962 A | 2/1998 |
| JP | 10-127346 A | 5/1998 |
| JP | 2001-309820 A | 11/2001 |
| JP | 2003-164334 A | 6/2003 |
| JP | 2004-041684 A | 2/2004 |
| JP | 2004-105705 A | 4/2004 |
| JP | 2004-321765 A | 11/2004 |
| JP | 2010-213908 A | 9/2010 |
| KR | 10 20030084978 A | 11/2003 |
| KR | 1020080054353 | 6/2008 |
| KR | 1020100068477 A | 6/2010 |
| WO | WO 96/36393 A1 | 11/1996 |
| WO | WO 02/071971 A1 | 9/2002 |
| WO | WO 02/071972 A1 | 9/2002 |
| WO | WO 2004/001948 A1 | 12/2003 |
| WO | WO 2005/062710 A2 | 7/2005 |
| WO | WO 2006/043758 A1 | 4/2006 |
| WO | WO 2006/046543 A1 | 5/2006 |
| WO | WO 2006/087927 A1 | 8/2006 |
| WO | WO 2006/104463 A1 | 10/2006 |
| WO | WO 2007/047568 A1 | 4/2007 |
| WO | WO 2007/072430 A3 | 10/2007 |
| WO | WO 2010/106850 A1 | 9/2010 |
| WO | WO 2011/013533 A1 | 2/2011 |
| WO | WO 2011/077290 A1 | 6/2011 |
| WO | WO 2011/077299 A1 | 6/2011 |
| WO | WO 2011/083793 A1 | 7/2011 |

OTHER PUBLICATIONS

International Search Report for PCT/US2012/056176, dated Dec. 10, 2012.
International Search Report for PCT/US2012/056175, dated Dec. 14, 2012.
International Search Report for PCT/US2012/056177, dated Dec. 18, 2012.
International Search Report for PCT/US2012/055279, dated Dec. 14, 2012.

* cited by examiner

THERAPEUTIC MICRO-CURRENT DELIVERY DEVICES AND METHODS THEREOF

TECHNICAL FIELD

The present application relates generally to iontophoresis devices and, more specifically, to therapeutic micro-current delivery devices, oral care devices, and methods that provide for increased micro-current delivery to a patient.

BACKGROUND

Iontophoresis is a medical technique that utilizes a small current (or charge) to deliver medicine or chemicals through the skin of a patient. Iontophoresis applications are numerous and may be used to treat many afflictions such as arthritis, warts, herpes and many others. Recently, iontophoresis is being used in oral care devices such as tooth brushes to aid in removing plaque from the teeth of uses as well as increase the delivery of fluorine negative ions to the teeth. Typical oral care devices that deliver ionic micro-currents are limited to about 80 µA because current levels over 80 µA has been shown to cause unpleasant sensations in users, such as pain, an electrical feeling and/or sour tastes. However, experimental data suggests that ionic current levels less than 80 µA provide minimal or no therapeutic benefits in oral care iontophoresis applications. Increased ionic current levels in iontophoresis devices and systems outside of oral care applications may also be desirable to increase the efficacy of such devices and systems.

Accordingly, alternative therapeutic micro-current delivery devices, oral care devices, and methods that enable increased ionic micro-current levels without causing unpleasant sensations in users of such devices and methods are desired.

SUMMARY

In one embodiment, a therapeutic micro-current delivery device includes a first electrode operable to be in electrical contact with a user at a first user location, a second electrode operable to be in electrical contact with the user at a second user location, a power source operable to provide a first voltage potential at the first electrode and a second voltage potential at the second electrode, and a micro-current control circuit in electrical communication with the first electrode, the second electrode and the power source. Electrical contact of the first electrode at the first user location and electrical contact of the second electrode at the second user location completes an electrical circuit between the first electrode and the second electrode. Upon a completion of the electrical circuit, the micro-current control circuit generates a micro-current $I_{ramped}$ through a user between the first user location and the second user location that increases from a start current $I_{start}$ to an end current $I_{end}$ over a rise time $t_{rise}$.

In another embodiment, an oral care device includes a handle portion, a brush head portion coupled to the handle portion, the brush head portion comprising brush filaments, a second electrode located in the handle portion and operable to be in electrical contact with a user at a first user location, and a first electrode located in the brush head portion and operable to be in electrical contact with an oral cavity of the user at a second user location. The oral care device further includes a power source operable to provide a first voltage potential at the first electrode and a second voltage potential at the second electrode and a micro-current control circuit in electrical communication with the first electrode, the second electrode and the power source. Electrical contact of the first electrode at the first user location and electrical contact of the second electrode at the second user location completes an electrical circuit between the first electrode and the second electrode. Upon a completion of the electrical circuit, the micro-current control circuit generates a micro-current through a user between the first user location and the second user location, the micro-current having a maximum value that is greater than 100 µA.

In yet another embodiment, a method of administering a therapeutic micro-current to an oral cavity of a user includes providing an oral care device having a second electrode in a handle portion and a first electrode in a brush head portion, providing a power source operable to produce a first voltage potential at the first electrode and a second voltage potential at the second electrode. Upon an electrical connection between the first electrode and a first user location of the user and a concurrent electrical connection between the second electrode and an oral cavity of the user, the method further includes generating a micro-current $I_{ramped}$ through a user between the first user location and the oral cavity that increases from a start current $I_{start}$ to an end current $I_{end}$ over a rise time $t_{rise}$.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

DETAILED DESCRIPTION OF THE INVENTION

Embodiments disclosed herein are generally related to therapeutic micro-current delivery devices and methods that deliver a micro-current to a patient. For example, such therapeutic micro-current delivery devices and methods may be implemented in iontophoresis applications in which micro-currents are applied to a patient to deliver a drug, substance, agent, or to produce a therapeutic effect. Generally, the embodiments disclosed herein enable the level of micro-current that is applied to a user (or patient) to be increased without the user experiencing an unpleasant sensation that may normally be associated with such a level of micro-current. More specifically, embodiments described herein utilize a ramping current control that increases the level of micro-current from a start current to an end current over a period of time.

Embodiments may be implemented in a device having a first electrode that is held by the user or is otherwise in electrical contact with some region of the user's body, and a second electrode that is to be applied at the region of iontophoretic interest (e.g., the oral cavity of a user). Micro-current flows through the user's body between the regions of the body that are in contact with the first and second electrodes because the user's body completes an electric circuit between the first and second electrodes. The effect of the ramping current control is to limit the sensation experienced by the user. For example, in an oral care application, the ramping current control lowers the voltage drop within the oral cavity. Various embodiments of the therapeutic micro-current delivery devices and methods are described in detail below.

Although the embodiments are described herein in the context of an oral care device, such as an electric toothbrush or a tongue cleaner, embodiments are not limited thereto. Embodiments disclosed herein may be implemented in a wide-variety of iontophoresis applications, such as in the application of idoxuridine in the treatment of herpes labilais, the application of methyl prednisolone sodium succinate in the treatment of apthous ulcers, the application of copper sulfate in the treatment of foot fungus, the application of salicylate in the treatment of warts, application of anti-inflammatory medications, diagnosis of cystic fibrosis, treatment of various dermatological conditions, cosmetic applications, and many others.

Figure 1:
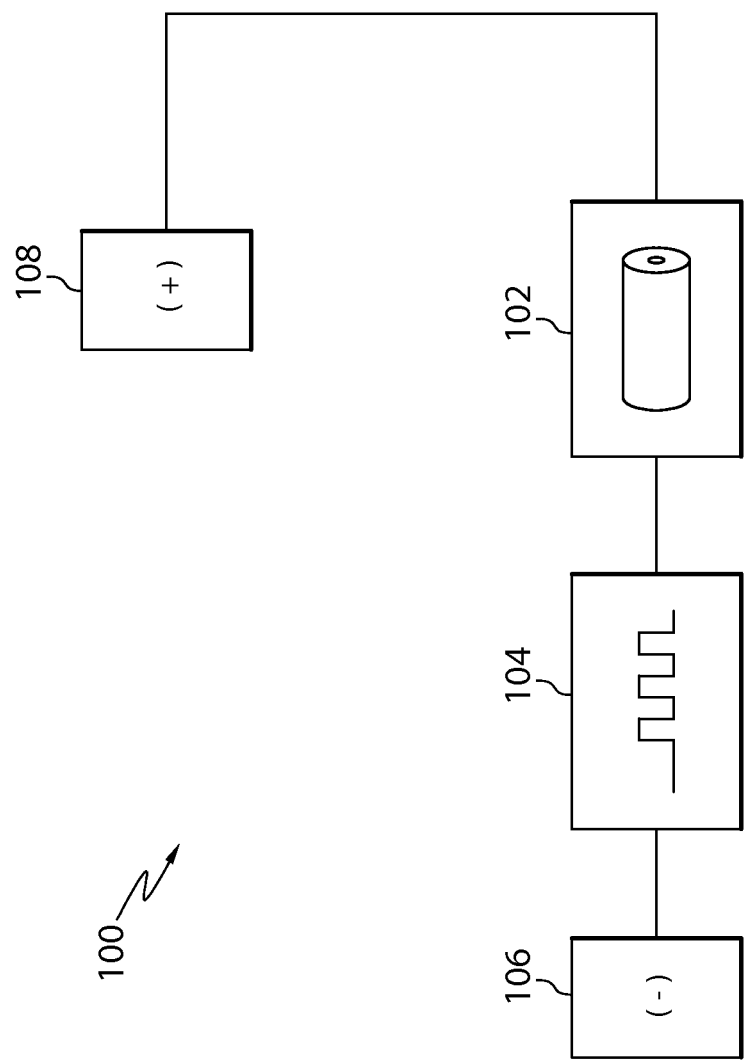
FIG. 1 schematically depicts electrical components of a therapeutic micro-current delivery device according to one or more embodiments illustrated and described herein.

Referring now to FIG. 1, a general schematic of some of the components of one embodiment of a therapeutic micro-current delivery device 100 is illustrated. The therapeutic micro-current delivery device 100 generally comprises a power source 102, a micro-current control circuit 104, a first electrode 106 and a second electrode 108. The power source 102 may be any power source capable of producing micro-currents (ionic) according to the particular application in which the therapeutic micro-current delivery device 100 is implemented. As an example and not a limitation, in an oral care device application, the power source 102 may comprise a battery capable of providing micro-currents in the range of 50 to 1000 µA. The power source 102 may also be an AC-DC converter circuit, DC-DC voltage regulator circuit, or any appropriate circuit to obtain the voltage levels and micro-current levels particular to the iontophoresis application. As an example and not a limitation, in an oral care application, the power source 102 may produce a voltage potential of about 30 volts to increase the iontophoresis effect and overcome the high electrical resistance of the human body portion of the electrical (ionic) circuit.

The first and second electrodes 106, 108 are electrodes that are configured to be in electrical contact with one or more locations of a user's body. Accordingly, the first and second electrodes 106, 108 should be electrically conductive. In one embodiment, the first and second electrodes 106, 108 are made of a metallic material. In another embodiment, the first and/or second electrode 106, 108 may be a touch electrode comprising a non-metal material filled with carbon filling as described in U.S. patent application Ser. No. 12/014,487 entitled "Oral Care Device" (e.g., carbon fibers that are dispersed in a non-electrically conductive resin such as ABC resin). It is noted that although the first electrode is illustrated as being associated with a negative polarity (−) and the second electrode is illustrated as being associated with a positive polarity (+), embodiments are not limited thereto. The first electrode may be associated with a positive polarity and the second electrode may be associated with a negative polarity.

Figure 5A:
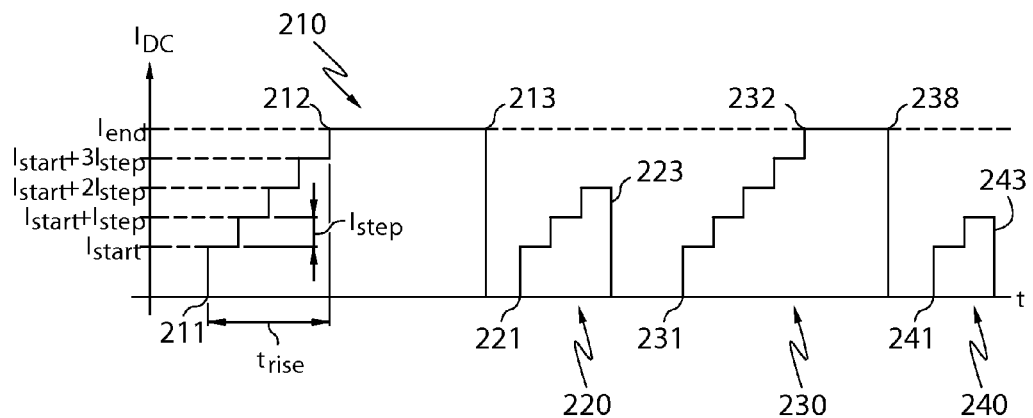
FIG. 5A graphically depicts a direct current ramping micro-current method according to one or more embodiments illustrated and described herein.
Figure 5B:
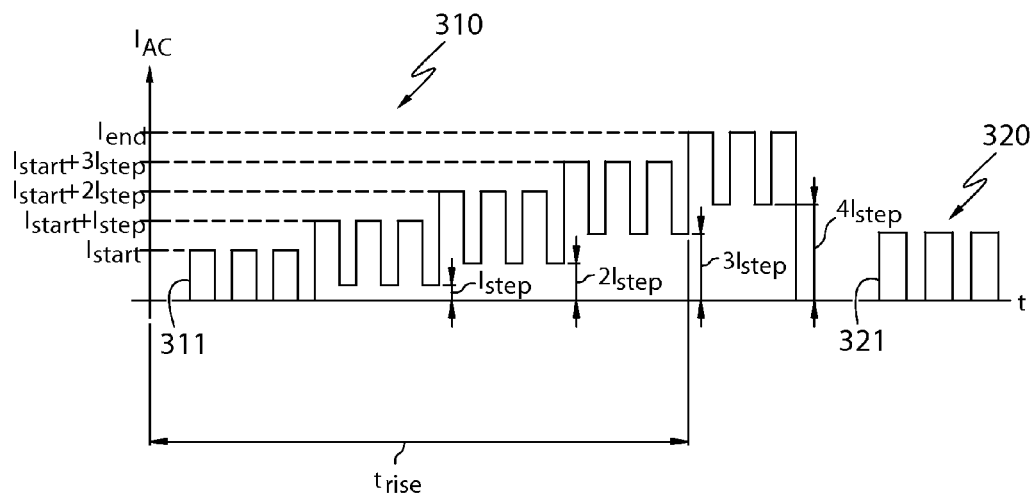
FIG. 5B graphically depicts an alternating current ramping micro-current method according to one or more embodiments illustrated and described herein.
Figure 5C:
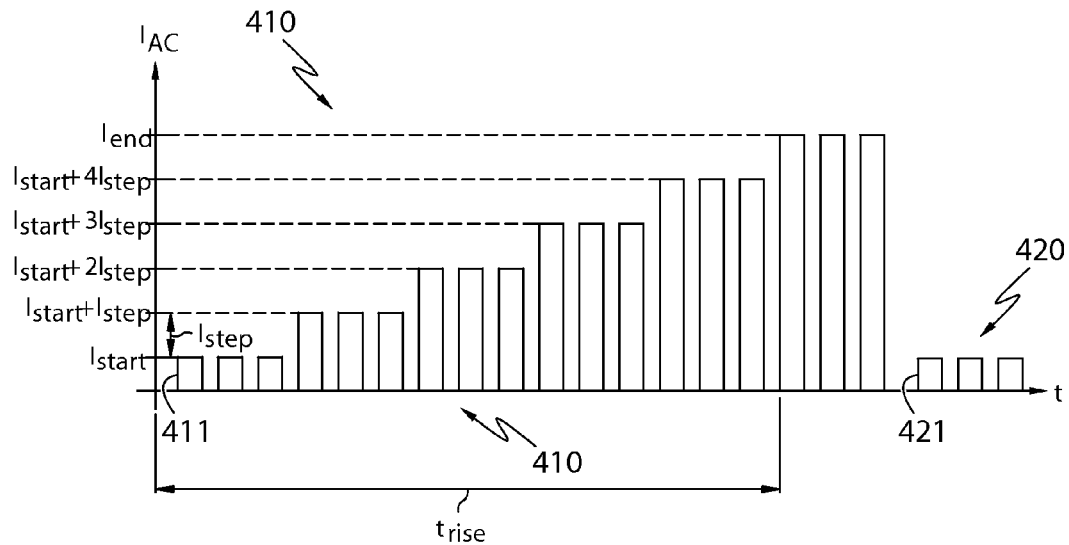
FIG. 5C graphically depicts an alternating current ramping micro-current method according to one or more embodiments illustrated and described herein.

The micro-current control circuit 104 is a circuit that is capable of providing ionic current upon completion of an electrical circuit through the body of a user at the desired micro-current levels. Further, the micro-current control circuit 104 effectuates the ramping control of micro-current that is applied to the user to limit the sensation that is experienced by the user. For example, FIGS. 5A-5C depict exemplary micro-current control methods that may be produced by the current control circuit 104. These micro-current control methods, as well as the current control circuit 104, will be described in greater detail below.

Figure 2:
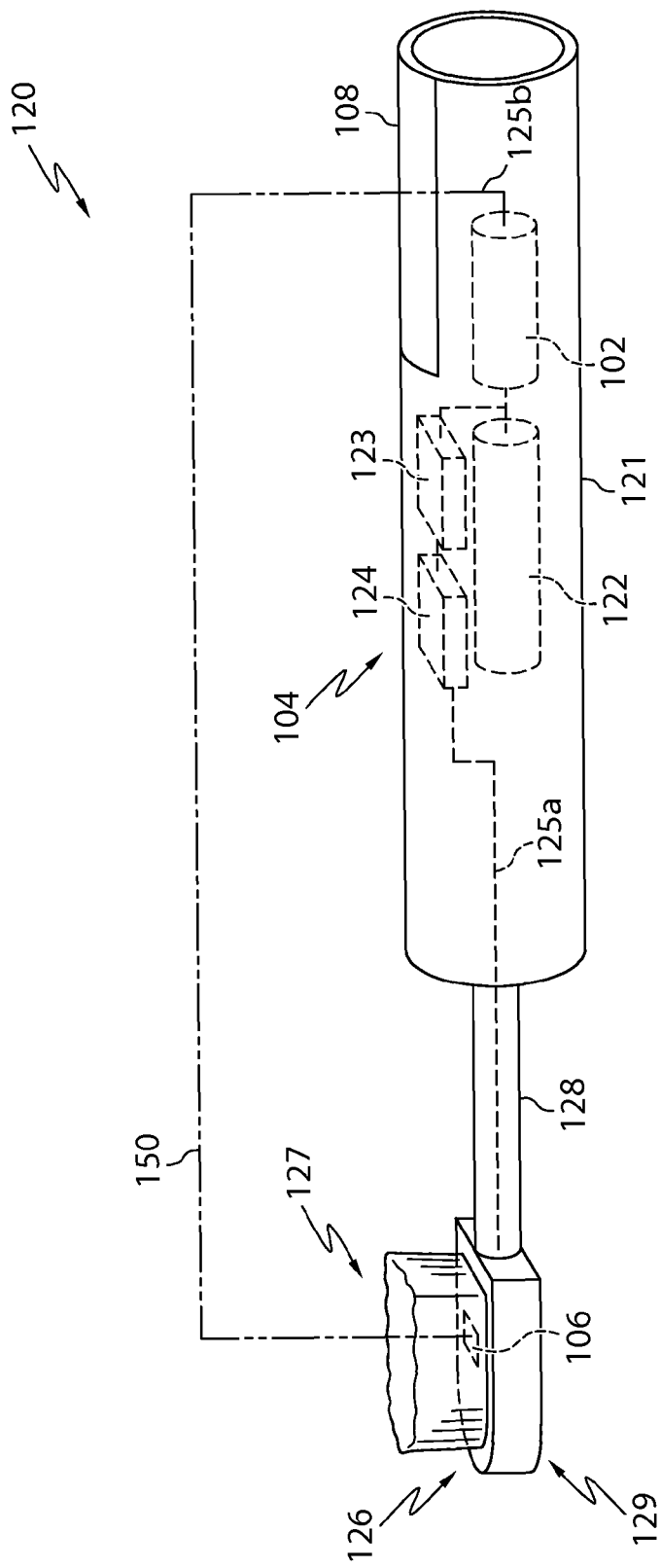
FIG. 2 schematically depicts a therapeutic micro-current delivery device according to one or more embodiments illustrated and described herein.

FIG. 2 depicts a graphical illustration of a therapeutic micro-current delivery device implemented as an oral care device 120. It should be understood that the arrangement of the components of the oral care device 120 is for illustrative purposes only and embodiments are not limited to such arrangement of components or configurations of the illustrated oral care device 120. The oral care device 120 comprises a body housing 121 and an oral care implement 126. The body housing 121 defines a handle portion on a first end of the oral care device 120. The oral care implement 126 is coupled to the body housing 121 defining a second end of the oral care device 120. In one embodiment, the oral care implement 126 is removably coupled to the body housing 121 such that oral care implements of differing configurations may be attached to the body housing 121 (e.g., a tongue cleanser or a flossing implement). In an alternative embodiment, the oral care implement 126 is not removable from the body housing 121 such that the body housing 121 and the oral care implement 126 are one integral component. The body housing 121 may be made of non-electrically conductive material, such as molded plastic, for example.

The illustrated oral care implement 126 generally comprises a stem portion 128 and a brush head portion 129 that is configured as an electric toothbrush head having toothbrush bristles 127 associated therewith. Both the stem portion 128 and the brush head portion 129 may be made of a non-electrically conductive material, such as a plastic material. The oral care implement 126 has a first electrode 106 that may comprise one or more electrically conductive regions. In the illustrated embodiment, the first electrode 106 comprises an electrically conductive pad that is located within an opening of the brush head portion 129 such that the electrically conductive pad of the first electrode 106 is exposed to the oral cavity of a user during operation of the oral care device 120.

As illustrated in FIG. 2, the second electrode 108 is provided in the body housing 121 such that it may be in electrical contact with the hand of a user when the user grips the body housing 121 to operate the oral care device 120. As described above, the second electrode 108 may be made of metallic material, a non-conductive resin with conductive carbon fibers dispersed therein, or any other electrically conductive material. It should be understood that embodiments are not limited to the configuration of the second electrode illustrated in FIG. 2. In one embodiment, an optional vibrating actuator 122 is provided and coupled to the power source 102. The vibrating actuator 122 may be configured to oscillate at a high frequency to provide vibration to the oral care device 120. The body housing 121 may also comprise other components, such as ON/OFF buttons or switches, mode selection buttons or switches, etc.

Maintained within the body housing 121 are various electrical components that produce the therapeutic ionic micro-currents. The power source 102 (i.e., a battery) is positioned within the housing with a first polarity (e.g., a positive polarity) of the power source 102 electrically coupled to the second electrode 108. The opposite polarity (e.g., a negative polarity) of the power source 102 is electrically associated with the first electrode 106 in the oral care implement 126 through the micro-current control circuit 104. Again, the polarity associated with the first and second electrodes 106, 108 may be reversed depending on the particular application.

The micro-current control circuit 104 may be mounted on a printed circuit board or other structure within the body housing 121. As shown in FIG. 2, the micro-current control circuit 104 may comprise a pulse generation circuit 123 and a pulse drive circuit 124. The pulse generation circuit 123 and pulse drive circuit 124 are illustrated at two physically separate circuits but it should be understood that the two circuits may be implemented in a single circuit in some embodiments. The pulse generation circuit 123 may generate the waveforms that are desired to be applied to the user, and the pulse drive circuit 124 may amplify the waveforms to have the appropriate current values for the particular iontophoresis application. Exemplary waveforms are depicted in FIGS. 5A-5C.

It is noted that in some iontophoresis applications, the electronics associated with generating the ramped micro-currents may not be maintained within a housing of the therapeutic micro-current delivery device 100 but rather in a separate enclosure that is electrically coupled to the therapeutic micro-current delivery device 100 held by the user.

An electric (ionic) circuit is provided by the electrical connection between the negative polarity of the power source 102 and the micro-current control circuit 104, the micro-current control circuit 104 and first electrode 106 (depicted by dashed line 125a), the positive polarity of the power source 102 and the second electrode 108 (depicted by dashed line 125b), and the conductive path between a hand and the oral cavity of the user (depicted by dashed line 150). The circuit is made when the user grips the first electrode 106 of the oral care device 120 and places the brush head 126 and first electrode 106 in his or her mouth. The circuit is opened when the user removes the brush head 126 and the first electrode 106 from his or her mouth. More generally, the circuit is made when a user grips a second electrode 108 of a therapeutic micro-current delivery device 100 and applies the first electrode 106 of the therapeutic micro-current delivery device 100 to a region of his or her skin (e.g., a foot to remove a plantar wart by application of salicylate through iontophoresis).

Figure 3:
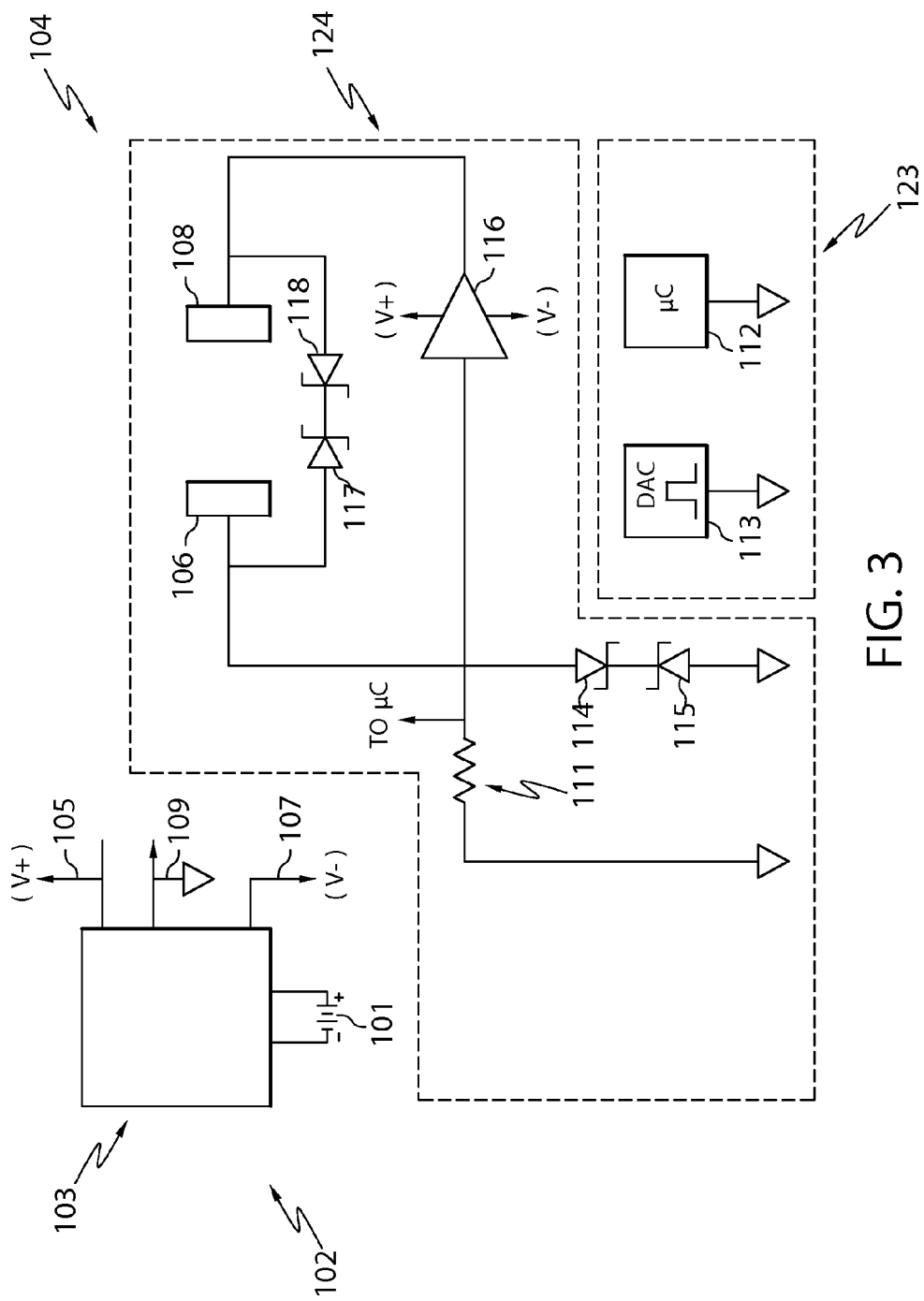
FIG. 3 schematically depicts a power source circuit and a micro-current control circuit according to one or more embodiments illustrated and described herein.

Referring now to FIG. 3, a schematic of the micro-current control circuit 104 and the power source 102 according to one embodiment is depicted. It should be understood that other circuits or modifications to the circuits illustrated in FIG. 3 may be used to produce the ionic micro-current waveforms that are depicted in FIGS. 5A-5C, and embodiments are not limited to the schematics of FIG. 3. The power source 102 of the illustrated embodiment comprises a battery 101 and a voltage regulator 103. The voltage regulator 103 receives the voltage of the battery 101 and provides a ground reference potential 109, a positive power rail potential 105 (V+) with respect to the ground reference potential (e.g., +30V), and a negative power rail 107 (V−) with respect to the ground reference potential (e.g., −30V). It should be understood that other voltage potentials may be utilized. The positive power rail potential 105 and the negative power rail potential 107 are provided to apply anodic or cathodic polarities. The voltages provided by the voltage regulator 103 may vary depending on the particular iontophoresis application. The circuit depicted in FIG. 3 and the described voltages are for an oral care application (e.g., tooth brushing, gum cleaning, and tongue cleaning).

The micro-current control circuit 104 generally comprises a pulse generation circuit 123 and a pulse drive circuit 124. The micro-current control circuit 104 may be any circuit that is capable of producing the waveforms of the ramping current control (e.g., those illustrated in FIGS. 5A-5C) at the particular frequencies, duty cycles, current levels, etc.

In one embodiment, the pulse generation circuit 123 comprises a microcontroller 112 and a digital-to-analog converter circuit or chip 113 (DAC) that cooperate to create a waveform that corresponds to the therapeutic micro-current that is to be applied to the user. The waveforms produced by the pulse generation circuit 123 are amplified by the pulse drive circuit 124 and therefore may have voltages that are less than that necessary to produce the desired micro-currents. For example, the voltages of the waveform pulses may be in a range between zero and a logic voltage level of the microcontroller. The microcontroller 112 may provide instructions to the digital-to-analog converter 113 to produce the pulses that make up the waveforms. The waveforms may be produced in a manner other than the illustrated pulse generation circuit 123. For example, the waveforms may be produced by a computer having a digital-to-analog converter card, or by a function generator, for example.

As stated above, the pulse drive circuit 124 is configured to amplify the waveforms provided by the pulse generation circuit 123 such that the desired micro-current levels (as well as desired frequencies and duty cycles) are applied to the user. The pulse drive circuit 124 comprises an operational amplifier 116 that receives the pulse train of the waveforms provided by the pulse generation circuit 123 as input and produces the therapeutic micro-currents as output. Accordingly, the operational amplifier 116 is used as a current source that amplifies the pulse trains of the waveforms. The operational amplifier 116 is electrically connected to the positive and negative power rails of the power source 102, and is electrically coupled to a current-sensing resistor 111 that is further coupled to the ground reference potential. The output of the operational amplifier 116 is electrically coupled to the first electrode 106, which, in the context of an oral care device, is to be positioned within the oral cavity of a user. The second electrode 108 is electrically coupled to the ground reference potential through the current-sensing resistor.

The current-sensing resistor 111 is provided to provide feedback of the ionic micro-current that is passed through the user to the microcontroller 112 to monitor and make adjustments to the micro-current levels provided to the user. In one embodiment, the current-sensing resistor 111 is a 1kΩ resistor such that 1 mV across the current-sensing resistor 111 corresponds to 1 µA.

In the embodiment illustrated in FIG. 3, the pulse generation circuit 123 and pulse drive circuit 124 may be protected by over-voltage protection devices. Zener diodes 117 and 118 clamp the voltage across the user to less than a user over-voltage value, such as 30V, for example. Zener diodes 114 and 115 protect the digital-to-analog converter 113 and microcontroller 112 by clamping the voltage to less than a pulse generation circuit over-voltage, such as 10V, for example.

In the oral care context, it is predicted that the administration of ionic current may be used to aid in the removal of plaque from the teeth and gums as well as administer fluorine ions to the teeth via iontophoresis. The ionic micro-current provided by the therapeutic micro-current delivery device 100 may flow from the brush head 126, across the saliva by the user to the mouth mucosa and/or teeth, across the body into the hand of the user, and back into the handle of the therapeutic micro-current delivery device 100.

Figure 4A:
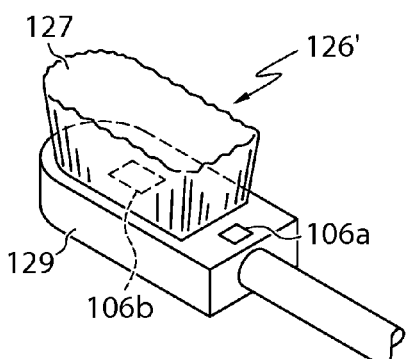
FIGS. 4A-4E schematically depict oral care implements of a therapeutic micro-current delivery device according to one or more embodiments illustrated and described herein.
Figure 4B:
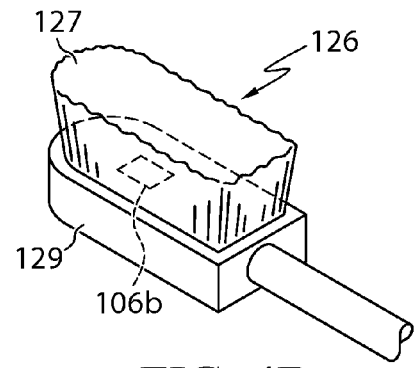
Figure 4C:
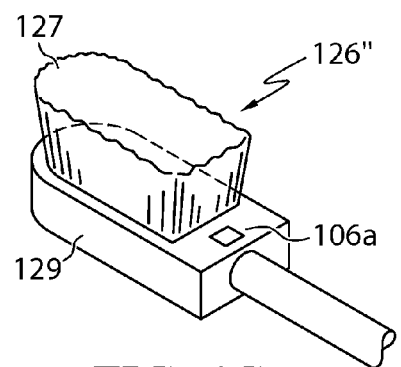

FIGS. 4A-4E illustrate various embodiments of oral care implements and first electrodes 106. The oral care implements and first electrode may take on a wide variety of configurations. It should be understood that embodiments are not limited to those configurations depicted in FIGS. 4A-4F. Referring to FIG. 4A, a brush head 126' is depicted having a first electrode that comprises a first conductive pad 106a that is positioned adjacent to the brush filaments 127, and a second conductive pad 106b that is positioned under the brush filaments 127. The brush head 126' depicted in FIG. 4A therefore provides two locations through which ionic current may flow. The brush head 126 depicted in FIG. 4B has a single conductive pad 106 positioned under the brush filaments 127, while the brush head 126" depicted in FIG. 4C has a single conductive pad 106" positioned adjacent to the brush filaments 127. It is also contemplated that the brush filaments 127 themselves may be electrically conductive and act as the first electrode.

Figure 4D:
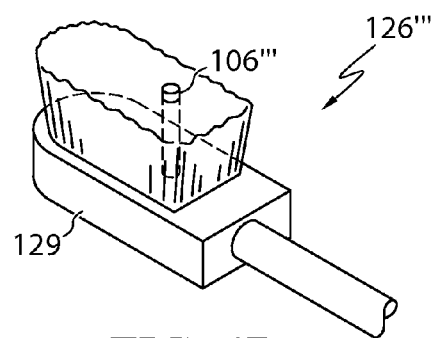
Figure 4E:
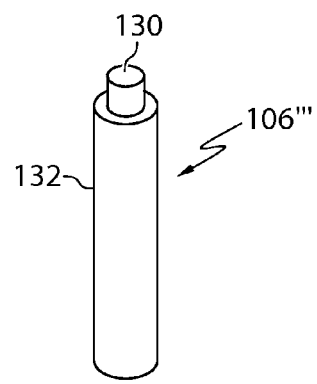

FIGS. 4D and 4E illustrate an embodiment in which the first electrode is in the form of one or more insulated conductor wires 106''' positioned amongst the brush filaments 127. FIG. 4E illustrates a close-up view of one embodiment of an insulated conductor wire 106''' shown in FIG. 4D. The insulated conductor wire 106''' comprises an electrically conductive wire core 130 that is made out of any electrically conductive material, such as a pliable metallic material, and an outer insulator jacket 132 that surrounds the electrically conductive wire core 130. The outer insulator jacket 132 is made of a non-conductive material that is sufficiently pliable to be used in a tooth brush application. A portion of the electrically conductive wire core 130 extends beyond the outer insulator jacket 132 such that it is exposed to the oral cavity of the user and may act as the first electrode as described above.

Figure 4F:
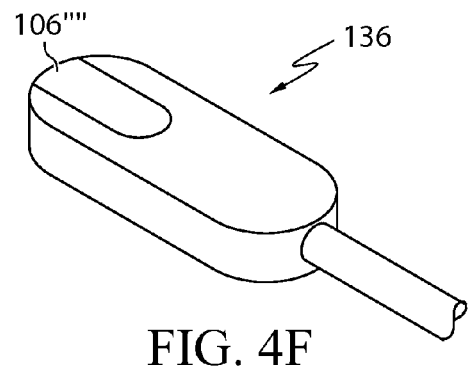
FIG. 4F schematically depicts an iontophoresis implement of a therapeutic micro-current delivery device according to one or more embodiments illustrated and described herein.

FIG. 4F illustrates one embodiment of an iontophoresis implement 136 that is configured to be applied to the skin of a user or a patient. The iontophoresis implement 136 comprises a first electrode 106'''' and may be used for a wide variety of iontophoresis applications. In another embodiment, the entire iontophoresis implement 136 is electrically conductive and is the electrode.

In one embodiment, the oral cavity of the user (teeth) is under positive voltage due to the positive first electrode 106, and the second electrode 108 of the brush head 126 is under negative voltage to direct flow of fluorine negative ions toward the positively charged teeth. Laboratory experiments suggest that the flow of fluorine ions directly depends on the level of micro-current that is delivered, and that higher current would be beneficial for greater delivery of fluorine ions and potentially for biofilm disruption. Experiments also indicate that pulsed ionic current of 80 µA (amplitude) or less provides little oral care benefit. However, higher current levels may cause unpleasant sensations for the user, such as an electrical feeling, pain, and/or a sour taste. The embodiments described herein enable the use of higher ionic current without the associated unpleasant sensations, and may therefore provide enhanced oral care efficacy.

Surprisingly, the present inventors have found that higher ionic current values may be applied to the oral cavity of users without unpleasant sensations by ramping the ionic micro-current from a start current $I_{start}$ to an end current $I_{end}$ over a rise time $t_{rise}$. Generally, when the circuit is made by the application of the first electrode 106 to the oral cavity of the user, the micro-current control circuit 104 produces a micro-current $I_{ramped}$ that starts at $I_{start}$ and increments to $I_{end}$ over $t_{rise}$, where it then is maintained at $I_{end}$ until the electrical circuit is opened by the removal of the first electrode 106 from the oral cavity of the user. Current ramping is repeated every single time the electric circuit is opened and closed. As described in more detail below, the end micro-current $I_{end}$ should be greater than about 100 µA, which is predicted to be the value of micro-current that increases brushing efficacy. In one embodiment, the end micro-current $I_{end}$ is between about 100 µA and about 800 µA. In another embodiment, the end micro-current $I_{end}$ is between about 400 µA and about 800 µA. The micro-current $I_{ramped}$ may be alternating current (AC) or direct current (DC) depending on the application. In AC applications, the micro-current ranges described above are amplitude micro-current values. It should be understood that the aforementioned micro-current ranges are intended for oral care applications, and other non-oral care applications may use different current ranges.

The time $t_{rise}$ should be long enough to minimize the sensation of the micro-current experienced by the user, but short enough such that the end micro-current $I_{end}$ is reached quickly so that the maximum current of the end micro-current $I_{end}$ is experienced by the user during the brushing session. As an example and not a limitation, the rise time $t_{rise}$ may be between 1 second and 20 seconds. Generally, the shorter the rise time $t_{rise}$, the greater the likelihood that a user will experience a sensation resulting from the micro-current. It is noted that it may be desirable for the therapeutic micro-current delivery device 100 to provide some sensation to the user so that the user may be aware that a micro-current is present and the therapeutic micro-current delivery device 100 is operating correctly. However, micro-currents and rise times that produce unpleasant sensations should be avoided. In one embodiment, the therapeutic micro-current delivery device 100 may be programmable by the user such that the user may select variables such as rise time $t_{rise}$, start current $I_{start}$, end current $I_{end}$, a step current $I_{step}$ (the amount of increased micro-current between increments), frequency, duty cycle, etc.

Referring now to FIG. 5A, one DC embodiment of a micro-current ramping waveform is illustrated (duty cycle equal 100%). Four exemplary micro-current pulse trains 210, 220, 230, and 240 are depicted. It should be understood that the graphs of FIGS. 5A-5C are provided for illustrative purposes. Each micro-current pulse train starts at contact between the first electrode and the oral cavity of the user (e.g., contact positions 211, 221, 231, and 241 of micro-current pulse trains 210, 22, 230, and 240 respectively). At each contact, the ramped micro-current $I_{ramped}$ starts at a start micro-current $I_{start}$. The start micro-current $I_{start}$ may be a current value that is known to not produce a sensation by the user. As a non-limiting example, the start micro-current $I_{start}$ may be 80 μA. The ramped micro-current $I_{ramped}$ then is incremented by the step current $I_{step}$ until the end current $I_{end}$ is reached after the rise time $t_{rise}$. For clarity, the "phrase ramped micro current $I_{ramped}$" means all of the components of the micro-current applied to the user, including the micro-current applied during the rise time $t_{rise}$ as well as the micro current that is applied after the rise time $t_{rise}$. The step frequency of the increments depends on the rise time $t_{rise}$ and the end current $I_{end}$. As an example and not a limitation, step current $I_{step}$ may be equal to about 80 μA In one embodiment, the ramped micro-current $I_{ramped}$ may not increment by $I_{step}$ but increase linearly as a continuous-time signal rather than in discrete steps.

After the rise time $t_{rise}$ at point 212 (and point 232), the ramped micro-current $I_{ramped}$ is maintained at the end current value $I_{end}$ until the electrical circuit is opened (e.g., at points 213, 223, 233, and 243). In some cases, the end current value $I_{end}$ may not be reached because the user opens the circuit prior to the rise time $t_{rise}$, as is illustrated by micro-current pulse trains 220 and 240.

FIG. 5B illustrates an AC embodiment of a micro-current ramping method. The operational duty cycle illustrated in FIG. 5B is 50%. However, AC embodiments may have an operational duty cycle other than 50%. For example, in one embodiment the duty cycle is variable between about 10% and 100% (DC micro-current). The frequency of the pulsed ramped micro-current $I_{ramped}$ may depend on the particular application. In one embodiment, the frequency of the pulsed ramped micro-current $I_{ramped}$ is about 9 kHz. Other frequencies may be utilized.

One full micro-current pulse train 310 and one partial micro-current pulse train 320 is illustrated in FIG. 5B. As described with respect to the embodiment illustrated in FIG. 5A, the micro-current starts at start micro-current $I_{start}$ when electrical contact is made between the first electrode and the oral cavity of the user (e.g., at point 311 and point 321). At first contact, the micro-current alternates between $I_{start}$ and zero μA. The micro-current is shifted by an offset amount $I_{step}$ such that it alternates between $I_{step}$ and $I_{start}$ plus $I_{step}$. The micro-current shifts further by $I_{step}$ until the end micro-current $I_{end}$ is reached. The values of the ramped micro-current $I_{ramped}$ over time may be expressed as alternating between $(0+(m-1)I_{step})$ and $(I_{start}+(m-1)I_{step})$ at an operational duty cycle (e.g., 50%), where m=1 upon a completion of the electrical circuit and increments by one at a step frequency until $(I_{start}+(m-1)I_{step})=I_{end}$. After rise time $t_{rise}$, the ramped micro-current $I_{ramped}$ then alternates between $I_{end}$ and $(I_{end}-I_{start})$ at the operational frequency until the electrical circuit is opened.

The step frequency depends on the rise time $t_{rise}$ and the end current $I_{end}$. As an example and not a limitation, the start current $I_{start}$ and the step current $I_{step}$ may be 80 μA.

FIG. 5C illustrates another AC embodiment of a micro-current ramping method. The operational duty cycle illustrated in FIG. 5C is 50%. As described above with reference to FIG. 5B, AC embodiments may have an operational duty cycle other than 50%, and the frequency of the pulsed ramped micro-current $I_{ramped}$ may depend on the particular application. In one embodiment, the frequency of the pulsed ramped micro-current $I_{ramped}$ is about 9 kHz.

One full micro-current pulse train 410 and one partial micro-current pulse train 420 is illustrated in FIG. 5C. As described with respect to the embodiment illustrated in FIGS. 5A and 5B, the micro-current starts at start micro-current $I_{start}$ when electrical contact is made between the first electrode and the oral cavity of the user (e.g., at point 411 and point 421). At first contact, the micro-current alternates between $I_{start}$ and 0 μA. The ramped micro-current $I_{ramped}$ is shifted by an offset amount $I_{step}$ such that it alternates between 0 μA and $I_{start}$ plus $I_{step}$. The micro-current shifts further by $I_{step}$ until the end micro-current $I_{end}$ is reached. The values of the ramped micro-current $I_{ramped}$ over time may be expressed as alternating between 0 and $(I_{start}+(m-1)I_{step})$ at an operational duty cycle (e.g., 50%), where m=1 upon a completion of the electrical circuit and increments by one at a step frequency until $(I_{start}+(m-1)I_{step})$. After rise time $t_{rise}$, the ramped micro-current $I_{ramped}$ then alternates between $I_{end}$ and 0 at the operational frequency until the electrical circuit is opened.

Figure 5D:
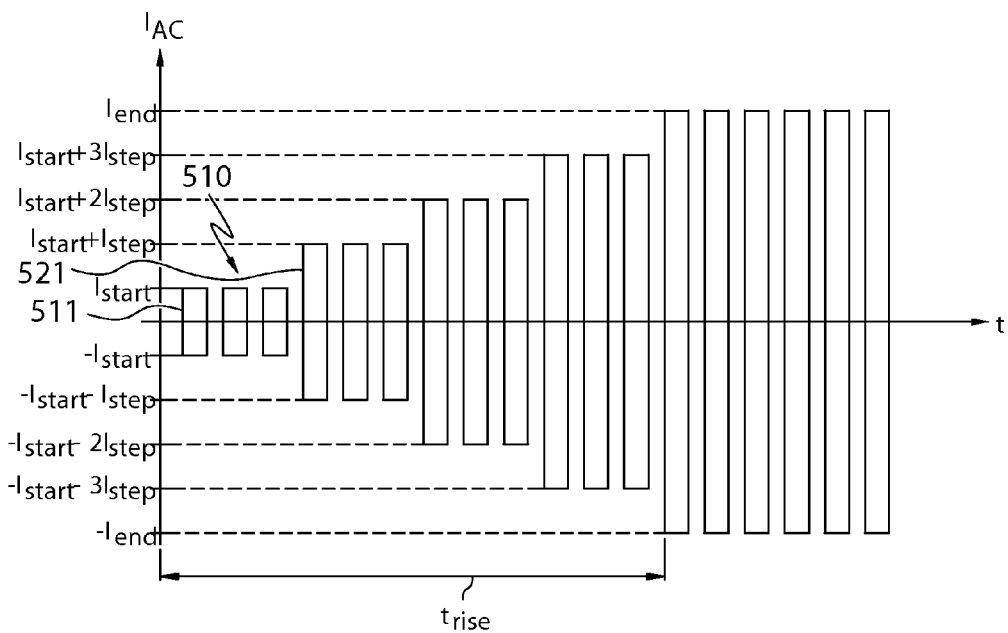
FIG. 5D graphically depicts an alternating current ramping micro-current method that switches between positive and negative currents according to one or more embodiments illustrated and described herein.

FIG. 5D illustrates another AC embodiment of a micro-current ramping method in which the pulses alternate between positive and negative micro-current values rather than switching between positive micro-current values and ground (i.e., zero micro-current). The micro-current pulse train 510 starts at start micro-current $+I_{start}$ when electrical contact is made between the first electrode and the oral cavity of the user (e.g., at point 511 and point 521 of pulse train 520). At first contact, the micro-current alternates between $+I_{start}$ and $-I_{start}$. In this manner, the micro-current alternates between positive and negative micro-current values. The ramped micro-current $I_{ramped}$ is shifted by an offset amount $I_{step}$ in both positive and negative directions such that it alternates between $(-I_{start}-I_{step})$ and $(I_{start}+I_{step})$. The micro-current shifts further by $\pm I_{step}$ until the end micro-current $I_{end}$ is reached. The values of the ramped micro-current $I_{ramped}$ over time may be expressed as alternating between $(-I_{start}-(m-1)I_{step})$ and $(I_{start}+(m-1)I_{step})$ at an operational duty cycle (e.g., 50%), where m=1 upon a completion of the electrical circuit and increments by one at a step frequency until $(I_{start}+(m-1)I_{step})=I_{end}$ and $(-I_{start}-(m-1)I_{step})=-I_{end}$. After rise time $t_{rise}$, the ramped micro-current $I_{ramped}$ then alternates between $+I_{end}$ and $-I_{end}$ at the operational frequency until the electrical circuit is opened.

Figure 5E:
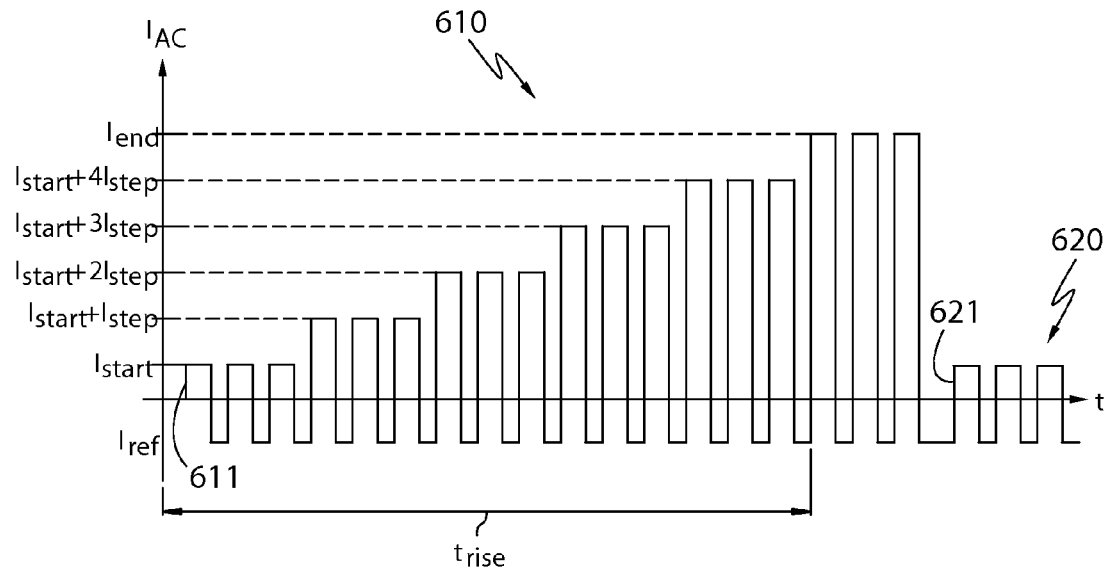
FIG. 5E graphically depicts an alternating current ramping micro-current method that switches between positive and negative currents according to one or more embodiments illustrated and described herein.

FIG. 5E illustrates yet another AC embodiment in which the pulses alternate between positive and negative micro-current values. The micro-current pulse train 610 starts at start micro-current $+I_{start}$ when electrical contact is made between the first electrode and the oral cavity of the user (e.g., at point 611 and point 621 of pulse train 620). At first contact, the micro-current alternates between $+I_{start}$ and $-I_{ref}$. $I_{ref}$ may be any micro-current value that is less than 0 μA. In one embodiment, $-I_{ref}$ is equal to $-I_{start}$. In this manner, the micro-current alternates between positive and negative micro-current values. The ramped micro-current $I_{ramped}$ is shifted by an offset amount $I_{step}$ in the positive micro-current direction such that it alternates between $(-I_{ref})$ and $(I_{start}+I_{step})$. The micro current shifts further by $I_{step}$ until the end micro-current $I_{end}$ is reached. The values of the ramped micro-current $I_{ramped}$ over time may be expressed as alternating between $(-I_{ref})$ and $(I_{start}+(m-1)I_{step})$ at an operational duty cycle (e.g., 50%), where m=1 upon a completion of the electrical circuit and increments by one at a step frequency until $(I_{start}+(m-1)I_{step})=I_{end}$. After rise time $t_{rise}$, the ramped micro-current $I_{ramped}$ then alternates between $-I_{ref}$ and $I_{end}$ at the operational frequency until the electrical circuit is opened.

A study was performed to evaluate the sensational tolerance of the ramped micro-current $I_{ramped}$ applied to subjects compared to micro-current that was not ramped upon electrical contact between the first electrode (the brush head) and the oral cavity of the subject. In a first part of the study, subjects brushed their teeth for 120 seconds using a 400 μA AC non-ramped micro-current $I_{non-ramped}$ operated at 9 kHz and 50% operational duty cycle. The first part of the study was compared with a second, third and fourth part of the study that provided a ramped micro-current $I_{ramped}$ in accordance with the ramping method depicted in FIG. 5C having $I_{end}$ currents of 400 μA, 600 μA and 800 μA, respectively. The step time ($I_{step}$) that the micro-current was incremented was 15 seconds, and the step current $I_{step}$ was 100 μA. The rise time $t_{rise}$ was 60 seconds for the 400 μA micro-current, 90 seconds for the 600 μA micro-current, and 120 seconds for the 800 μA micro-current.

The participants were asked to press a STOP button when they experienced an unpleasant sensation. Upon pressing the STOP button, the application of micro-current stopped immediately and software logged the event. 55.6% of the subject that experienced the non-ramped micro-current $I_{non-ramped}$ experienced one stop during the test. However, zero of the subjects that experienced the various ramped micro-currents (i.e., 400 μA, 600 μA and 800 μA) experienced a stop during the test. Additionally, of the subjects that logged a stop during the non-ramped micro-current test and also participated in the ramped micro-current tests, none logged a stop during the ramped tests.

Figure 6A:
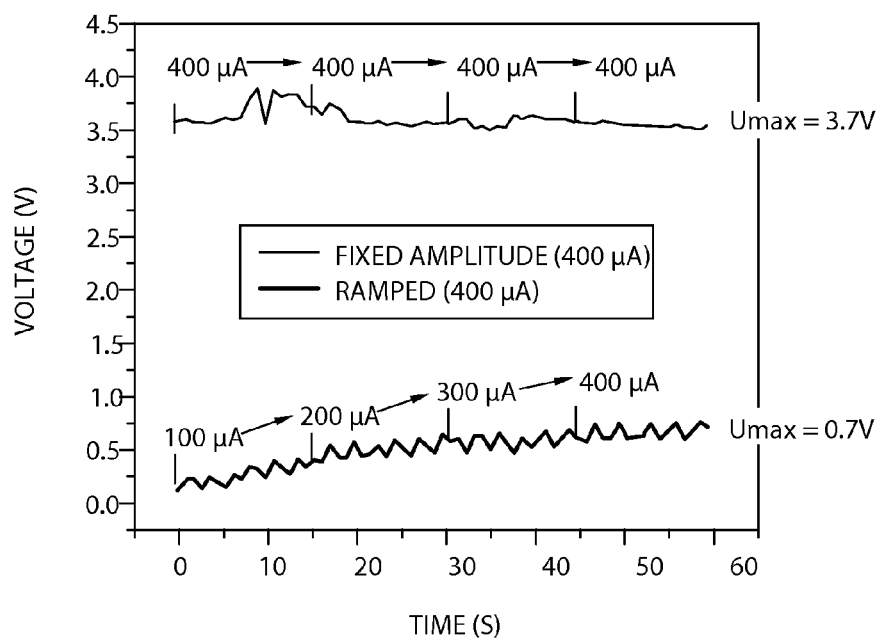
FIG. 6A graphically depicts a comparison of experimental voltage drop in the oral cavity of a user between non-ramped and ramped anodic micro-current with a 100% operational duty cycle.
Figure 6B:
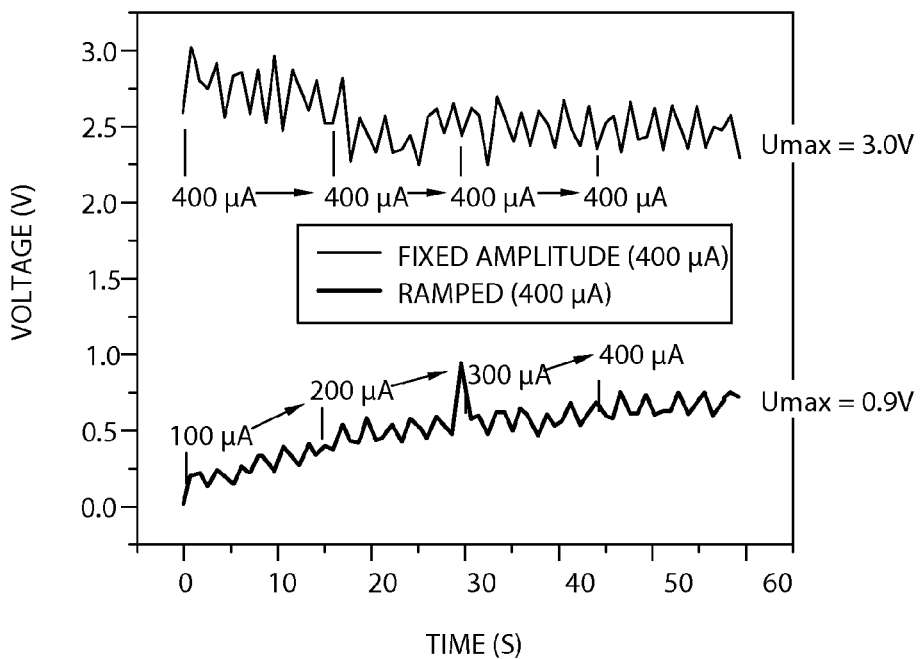
FIG. 6B graphically depicts a comparison of experimental voltage drop in the oral cavity of a user between non-ramped and ramped anodic micro-current with a 50% operational duty cycle.
Figure 6C:
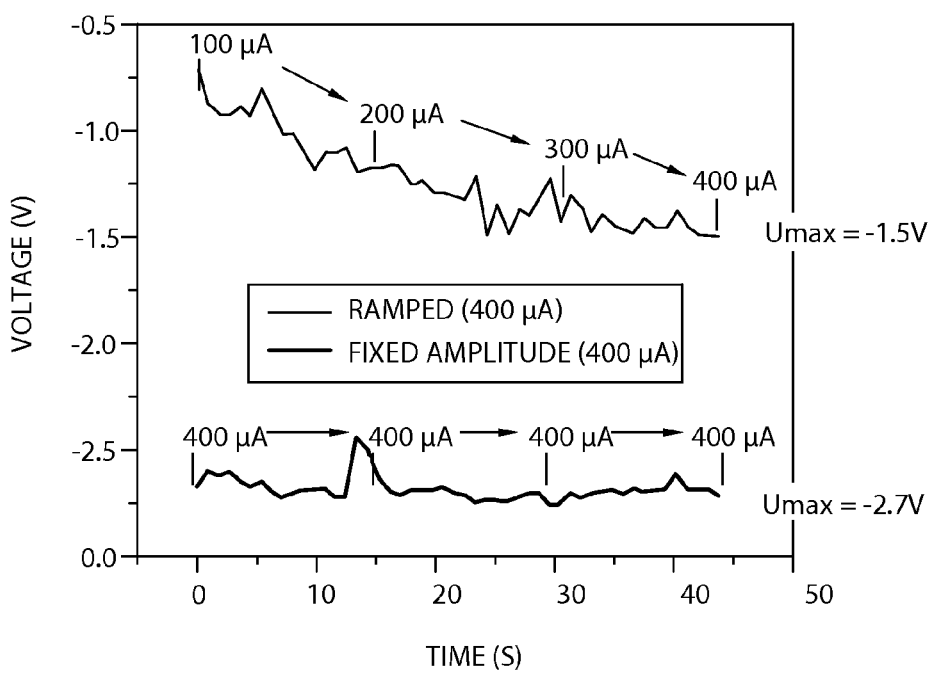
FIG. 6C graphically depicts a comparison of experimental voltage drop in the oral cavity of a user between non-ramped and ramped cathodic micro-current with a 100% operational duty cycle.
Figure 6D:
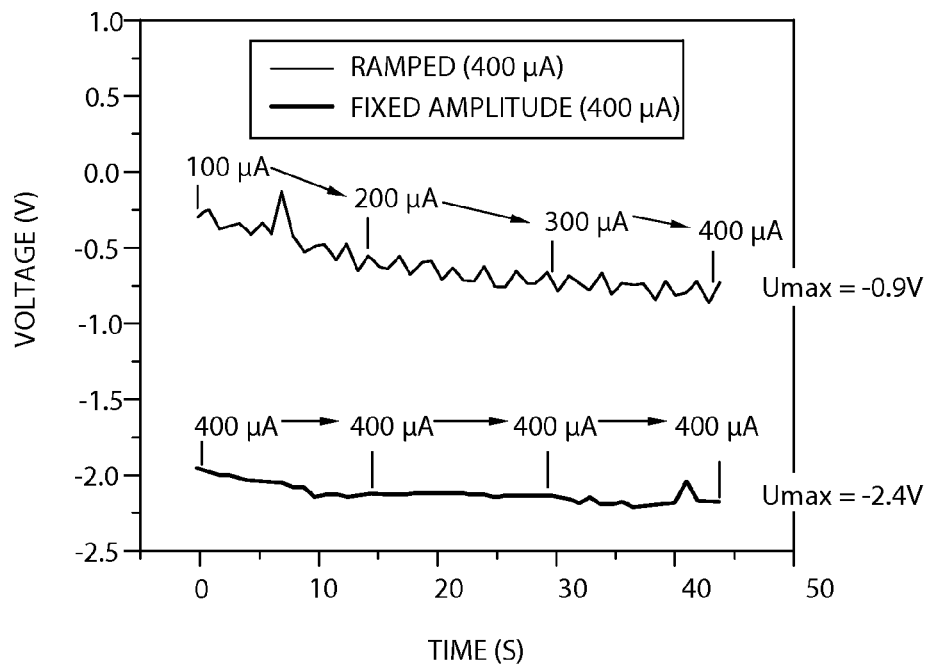
FIG. 6D graphically depicts a comparison of experimental voltage drop in the oral cavity of a user between non-ramped and ramped cathodic micro-current with a 50% operational duty cycle.

In-mouth voltage drop was also measured and compared for both non-ramped micro-current and ramped micro-current (100 μA to 400 μA in 100 μA increments over a 60 second time period), DC and AC micro-currents, and both anodic and cathodic polarity. To determine the in-mouth voltage drop, the potential drop between the brush head and the mouth was measured. Lower voltage drop is desired because of the electrochemical reaction that can occur in the saliva/dentifrice mixture. FIG. 6A illustrates the anodic results with a 100% duty cycle, FIG. 6B illustrates the anodic results with a 50% duty cycle, FIG. 6C illustrates the cathodic results with a 100% duty cycle, and FIG. 6D illustrates the cathodic results with 50% duty cycle.

Surprisingly, the results graphically illustrated in FIGS. 6A-6D show that the ramped micro-current method produces a lower voltage drop ($V_{ramped}$) than the non-ramped micro-current method ($V_{non-ramped}$) in each instance. The voltage drop of the ramped micro-current method is almost a factor of two lower than the non-ramped micro-current method. This is true for both polarities and the different duty cycles. The smaller user-sensations provided by the ramped micro-current method may be attributed to the lower voltage drop within the oral cavity. Accordingly, the use of ramped micro-current $I_{ramped}$ enables the therapeutic micro-current delivery device 100 to deliver ionic current at current levels greater than 100 μA with minimal user-sensation. The application of ionic current greater than 100 μA may provide for better oral care efficacy due to the increased micro-current level.

Although the therapeutic micro-current delivery device 100 and the associated ramping micro-current methods have been described in the context of an oral care device such as a tooth brush, embodiments are not limited thereto. For example, there are many oral care application other than a tooth brush that the embodiments described herein may be utilized. As examples and not limitations, ramped micro-current may be utilized for increased micro-current in dental iontophoresis applications such as treatment of dentinal hypersensitivity (2% NaF), herpes labilais (Idoxuridine), apthous ulcers (methyl prednisolone sodium succinate), anesthesia (pre-injection topical Lidocain), and teeth whitening (hypochlorite), among others Additionally, the embodiments described herein may be utilized in applications outside of dental iontophoresis. It is noted that the micro-currents described above (e.g., between 100 μA and 1000 μA) may be different in applications outside of dentistry and oral care. For example, in iontophoresis applications in which the first electrode is in contact with skin, the ionic current levels may be ten times greater than those ionic micro-currents described above with respect to contact between the first electrode and the oral cavity. Other parameters of the ramped micro-current may be different in applications outside of dentistry, such as operational duty cycle, frequency, AC or DC current, etc. Non-limiting examples of iontophoresis in medicine in which the ramped micro-current techniques of the embodiments described herein include treatment of inflammation of joints and arthritis (corticosteroids), skin anesthesia (Lidocain, epinephrine), arthritis (hyaluronidase, vasodilators, citrate/acetate), ischemic ulcers (zinc), foot fungus (copper sulfate), warts (salicylate), and lodex scare tissue (iodide). Embodiments may also be utilized in beauty care applications where micro-currents are used to smooth skin, remove blemishes, remove wrinkles, etc. The ability to increase the amount of micro-current delivered to the user may increase the efficacy of many of the aforementioned iontophoresis applications.

Comparative Study—Treatment of Plaque

A study was performed to evaluate the effect of ionic current in toothbrushes providing 80 μA of current on the treatment of plaque and oral malodor. The study was a single-center, single-brushing, four treatment, randomized, eight period crossover study. Twenty adult subjects were enrolled. The study consisted of an acclimation visit followed by eight periods (Periods 1-8). Digital Plaque Imaging Analysis (DPIA) was used to measure plaque coverage. The aim of the study was to determine the effect of ionic current in a toothbrush on delivery of cetylpyridnium chloride (CPC).

During the acclimation visit, subjects were given an acclimation toothbrush (Panasonic®Ionic Handle EW 1045 brush), a manual toothbrush, and acclimation toothpaste (Crest® Cavity Protection dentifrice (0.243% sodium fluoride)). Subjects brushed their teeth for two minutes at the study site under supervision for their first brushing. Subjects then used their acclimation products in place of their normal toothbrushes for two to three days, then switched to the manual toothbrush, but continued to use the acclimation toothpaste 48 hours prior to Period 1.

During Periods 1 through 8, the subjects used the manual toothbrush and acclimation toothpaste in between study visits. The subjects refrained from all oral hygiene procedures for 12 hours prior to their next appointment time (their last brushing was the evening (7:00 pm) prior to the scheduled visit day). Subjects also refrained from eating, drinking, chewing gum and smoking (including smokeless tobacco) for four hours prior to their next appointment time. Only small sips of water were permitted, with no sipping of water 60 minutes prior to the next measurement.

During Periods 1 through 7, each subject was randomly assigned to one of four treatments, which were as follows:

Treatment A: 30 second rinse with 20 ml of water followed by two minutes of brushing using a Panasonic® Ionic Handle EW-DE-40 experimental brush with a twin ionic brushhead (sonic on, 80 µA ionic (anodic) current on) and the acclimation toothpaste;

Treatment B: 30 second rinse with 20 ml of water followed by two minutes of brushing using a Panasonic® Ionic Handle EW-1045 experimental brush with a twin ionic brushhead (sonic on, ionic current off) and the acclimation toothpaste;

Treatment C: 30 second rinse with a solution comprising 5 ml of CPC in 20 ml water followed by two minutes of brushing using a Panasonic® Ionic Handle EW-DE-40 experimental brush with a twin ionic brushhead (sonic on, 80 µA ionic (anodic) current on) and the acclimation toothpaste; and Treatment D: 30 second rinse with a solution comprising 5 ml of CPC in 20 ml water followed by two minutes of brushing using a Panasonic® Ionic Handle EW-1045 experimental brush with a twin ionic brushhead (sonic on, ionic current off) and the acclimation toothpaste.

The subjects were supervised while performing the assigned oral hygiene sequences described above, and returned to an imaging lab between 2:00 and 3:00 pm in the afternoon for imaging. The subjects refrained from eating and drinking 60 minutes prior to the afternoon measurement. During the imaging session, each subject had a DPIA UV image taken in accordance with the following procedure:

Rinse for 10 seconds with 25 ml of phosphate buffer;
Rinse for 1 minute with 5.0 ml of 1240 ppm fluorescein in phosphate buffer;
Rinse 3 times for 10 seconds with 25 ml of phosphate buffer; and
Acquire DPIA UV image.

The photographic system used to take the DPIA UV image comprised a high-resolution digital camera having a 25 mm lens and a linear polarizer to permit cross-polarized light. A UV flash provided the lighting. The camera was connected to a personal computer, which recorded and analyzed the images. A digital image of the maxillary and mandibular anterior facial surfaces was captured. Tooth and plaque pixels were classified in the digital image and the percent plaque coverage on the teeth was calculated. For the examination, the lighting in the examination room was ambient. The subject sat on a stool in front of a chin rest used to hold the head still. Plastic retractors were used to retract his or her lips and cheeks. The incisal edges of the front teeth were placed together and centered in the camera. Prior to exposure, the subject drew air through his or her teeth and positioned his or her tongue away from the teeth so that the tongue was not visible.

During Period 8, the subjects were randomly assigned a treatment sequence as described above. The subject returned to the imaging lab between 2:00 and 3:00 pm and refrained from eating and drinking 60 minutes prior to the image measurement. During the imaging session of Period 8, each subject had a DPIA UV image taken in accordance with the following procedure:

Rinse for 10 seconds with 25 ml of phosphate buffer;
Rinse for 1 minute with 5.0 ml of 1240 ppm fluorescein in phosphate buffer;
Rinse 3 times for 10 seconds with 25 ml of phosphate buffer; and
Acquire DPIA UV image.

The mean percentage plaque coverage was generated for each subject in each treatment period. The plaque percentage was analyzed using an analysis of variance for crossover design with factors in the model for subject (random effect), period, carryover, rinse (water/cetylpyridnium chloride), and ionic power (on/off). All pairwise comparisons between the 4 treatment regimens were also carried out.

Results

Figure 7:
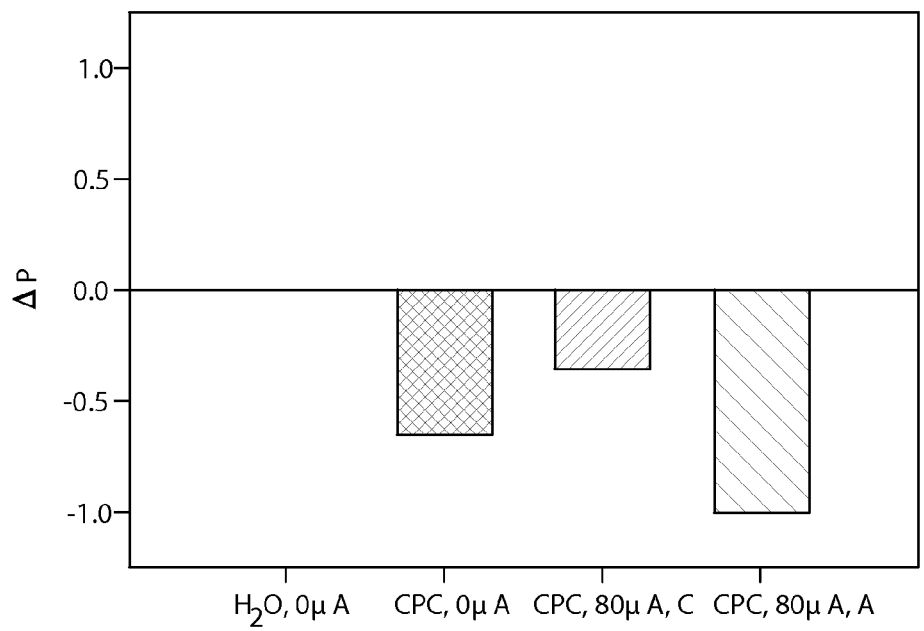
FIG. 7 is a chart that graphically depicts results of comparative study applying 80 µA of non-ramped micro-current.

FIG. 7 is a graph comparing change in plaque ($\Delta P$) resulting from water rinse with no ionic current (labeled "$H_2O$, 0 µA"), cetylpyridnium chloride (CPC) rinse with no ionic current (labeled "CPC, 0 µA"), CPC rinse with anodic ionic current (labeled "CPC, 80 µA, A"), and CPC rinse with cathodic ionic current (labeled "CPC, 80 µA, C"). The CPC rinse with no ionic current effect under the conditions was about a 5% relative plaque reduction (about $-0.64$ units of plaque coverage ($p-0.2$ vs. water).

Figure 9:
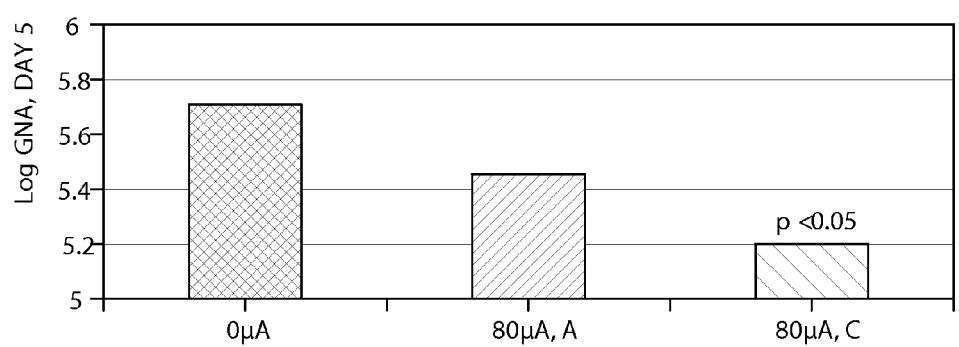
FIG. 9 is a chart that graphically depicts tongue sample GNA bacteria results on Day 5 of a study.

The anodic ionic current should make the oral cavity negatively charged and, theoretically, drive more CPC into the teeth. The graph of FIG. 9 illustrates that the anodic ionic current increases plaque reduction by an added amount over the CPC rinse with no ionic current—from about $-0.64$ to about $-0.98$ units ($p<0.5$ vs. water; $p-0.2$ vs. CPC control). However, the cathodic ionic current caused plaque reduction in the wrong direction which made the CPC rinse less effective than rinsing alone.

Accordingly, it has been shown that 80 µA anodic ionic current may provide some benefits when used in conjunction with a CPC rinse regimen.

Comparative Study—Oral Malodor

An oral malodor study comprising a single-center, three treatment, randomized, three period, cross-over design was conducted. Up to twenty adult subjects were enrolled. Generally, each treatment period of the study consisted of an acclimation/wash out period of up to three days prior to Day 1 of the study, a study-duration of five days, wherein Halimeter (breath) measurements were performed on Day 2, Day 3, and Day 5, and micro samplings of the tongue and oral lavage were collected on Day 1 and Day 5. Subjects completed three treatment periods using randomly assigned treatment products.

The Halimeter unit tests for volatile sulfur compounds (VSC). The Halimeter is sensitive to hydrogen sulfide and methyl mercaptan, two of the primary components of foul breath odor. A trained technician performed all Halimeter measurements. The Halimeter measurement procedures were as follows: The subjects were instructed to keep their mouth closed for two minutes. The subjects then placed a piece of barrier tape on the Halimeter board above the hole and then placed one end of a clean paper cylinder, about 1.75 inches long by 1¹⁄₁₆ inches in diameter, through the hole in the Halimeter board. Subjects were instructed to swallow, if they would like, 30-45 seconds prior to their Halimeter measurement, being sure to keep their mouth closed. After two minutes, the subjects were instructed to inhale through their nose and hold their breath. The technician recorded a background Halimeter value immediately before the subject approached the Halimeter. The subject then approached the Halimeter and, while holding their breath, placed their teeth and lips loosely around the tube. While the subjects held their breath, the instrument drew air from the mouth (without touching the subject's mouth) and the technician recorded the measured value indicated on the instrument. The subject then removed the barrier tape and the paper cylinder they used and discarded them in the appropriate receptacle.

During the acclimation period, subjects were given acclimation products consisting of an ADA reference manual toothbrush and Crest® Cavity Protection (4.6 oz) dentifrice (overtubed). Subjects brushed their teeth with their acclimation products twice a day for up to three days.

Throughout the study, subjects were instructed not to eat highly seasoned foods or foods associated with oral malodor (e.g., garlic) and not to drink alcohol anytime during the acclimation periods and each treatment period. Subjects were also to perform their evening brushing prior to 11:00 pm the night before their next scheduled visit (Day 1) and to refrain from any type of oral hygiene and from breath mints, medicated lozenges, eating, drinking (only small sips of water were permissible, with no drinking 45 minutes prior to the next measurement), smoking, chewing gum, or chewing tobacco after their evening brushing the night before their next appointment time.

Day 1

Subjects were given treatment kit boxes containing treatment products that included one treatment tooth brush (a Panasonic® Twin Ionic "AySy" brush handle EW-DE-40 (anodic), a Panasonic® Twin Ionic "CySy" brush handle EW-DE-40 (cathodic), or a Panasonic® Ionic handle EW 1045 brush handle), Crest® Cavity Protection (4.6 oz) dentifrice, and a Metback twin ionic brush head. The Metback twin ionic brush head has a conductive surface on a back side of the brush head (i.e., the surface of the brush head that is opposite from the side having the bristles). Additionally, the Metback twin ionic brush head has a first electrode positioned underneath the bristles and a second electrode positioned just below the bristles.

The treatment kit boxes were distributed based on a randomly assigned treatment sequence. The subjects used the same treatment product within the five day treatment period (Monday through Friday).

Microbiological tongue samples were taken from each subject by gently placing a new, clean toothbrush over the tongue either to the right or left half of midline with slight agitation of the bristles on the tongues surface for five seconds. Collection from right or left sides of the tongue was randomized across the entire panelist group. The brush was then transferred to a vial containing 10 mL of a microbial transport fluid (reduced Transport Fluid (RTF)) and the brush head was aseptically clipped off into the vial. The vial was then sealed and kept on ice until plating on microbiological media. A micro oral Lavage sample was then collected. Subjects were instructed to vigorously swish their mouth for 30 seconds with 10 mL of sterile USP water and spit it out into a collection tube. Tubes were sealed and stored on ice until plating on microbiological media. Microbiological samples were collected on Day 1 and Day 5 of each treatment period. The micro samples of the tongue and the oral lavage tested for gram negative anaerobes (GNA), total facultative anaerobes (TNA), and sulfur producers.

Subjects were instructed to brush with the treatment products by brushing their teeth and cleaning their tongue as instructed twice a day. For teeth brushing, the subjects were instructed as follows:
Securely attach brush head;
Grip the main body, with the hand touching the ion panel;
Wet brush head and apply enough paste to cover brush head;
Select a Mode (the first mode "powerful");
Before turning brush on, briefly spread toothpaste around teeth;
To avoid splashing, turn the operation switch on, while brush head is in mouth;
Move the brush head in a slightly circular motion, similar to a manual toothbrush;
After a few seconds, guide the bristles to the next section;
Finish brushing after one minute;
Upon completion of brushing, turn the brush off by pressing the operation switch;
Expectorate out excess toothpaste into basin.
Rinse out residual paste by swishing 10 ml of water in mouth for 10 seconds; and
Expectorate in basin.

For tongue brushing, the subjects were instructed as follows:
Place the back side of the brush head on tongue beginning in the back and turn the power on. Split the tongue into 2 sections (left and right of tongue midline). Beginning in the back left, clean the tongue with circular motion over the left side of tongue for 30 seconds. Repeat for right side for additional 30 seconds. Turn power off.
Expectorate any additional paste saliva into basin.
Perform final rinse with 10 ml of water by swishing for 10 seconds.

Subjects were rescheduled and asked to return two hours from the time they brushed. In addition, subjects were reminded to refrain from any type of oral hygiene and from eating, drinking, smoking or using breath mints, medicated lozenges, chewing gum or chewing tobacco until after their two hour post-brushing appointment. Then a two-hour micro sample, in accordance to a randomization chart, sample was taken from the opposite side of tongue midline from which the sample was previously collected in the same manner as described above. Immediately thereafter, oral lavage samples were also collected in the same manner as described above.

The treatment products stayed at the site (stored in kit boxes) and the subjects were instructed to continue with their acclimation products during the evening brushing.

Day 2

The subjects returned to the site with their acclimation kit boxes. A baseline (BL) Halimeter breath measurement was taken followed by: 1) standardized breakfast (bagel, cream cheese and water), 2) redistribution of treatment kit boxes, 3) review of brushing instructions, and 4) supervised brushing of teeth and tongue cleaning with the treatment products.

Subjects were rescheduled and asked to return three hours from the time they brushed. A three-hour Halimeter breath measurement was taken. Subjects were instructed to perform their evening brushing prior to 11:00 pm the night before their Day 3 visit.

Day 3

The subjects returned to the testing site without having performed any type of oral hygiene the morning of the Day 3 visit and without eating, drinking, or smoking, as described above. Approximately 24 hours after the subject's last BL breath measurement, a 24-hour Halimeter breath measurement was taken followed by a standardized breakfast, supervised brushing of teeth and tongue cleaning with the treatment products, as described above.

The subjects were rescheduled to return to the testing site three hours after brushing their teeth and tongue. A 27-hour Halimeter breath measurement was taken.

The subjects were instructed to follow the same brushing regimen at home: brushing teeth and cleaning tongue twice a day (morning and evening) with treatment products. The last (unsupervised) evening brushing prior to the study visit continued to be before 11:00 pm.

The subjects were rescheduled and reminded not to eat highly seasoned foods or foods associated with oral malodor, not to drink alcohol, etc.

Day 4

The subjects continued to use their treatment products at home as instructed (morning and evening usage).

Day 5

On Day 5, the subjects returned with their treatment kit boxes and breath measurements and micro samples were taken. The subjects had brushed their teeth prior to 11:00 pm the night before their scheduled visit with the treatment products.

The subjects had a Halimeter breath measurement followed by collection of micro samples (according to the procedures described previously). The subjects returned their treatment products and washout kit boxes were redistributed for washout between treatment periods. The subjects were rescheduled for Day 1 of the next treatment period and reminded not to eat highly seasoned foods or foods associated with oral malodor (i.e., garlic) and not to drink alcohol anytime during each treatment period, Monday through Friday of weeks that have study visits. In addition, the subjects were reminded to perform their evening brushing prior to 11:00 pm the night before their next scheduled visit (Day 1), and to refrain from any type of oral hygiene and from eating, drinking, smoking or using breath mints, medicated lozenges, chewing gum or chewing tobacco after their evening brushing the night before their next appointment time.

After the tongue and oral lavage samples were collected, they were maintained at 4° C. until same day processing (within 4 hours post sampled collection) by the trained microbiology personnel was performed. The estimate of bacteria recovered from the samples was determined and reported for each subject at each of the three sample time-points (BL, 2 hrs. post treatment on Day 1 and post treatment on Day 5).

Analysis

Volatile sulfur compounds measured by the Halimeter were analyzed on the natural logarithm scale prior to any statistical analysis. Mean results were transformed back to the original scale. Overnight (24 hour time point) Halimeter data was analyzed for treatment differences using analysis of covariance (ANCOVA) for crossover studies. The ANCOVA model included subject (random), period, treatment and, if statistically significant at the 10% level, carryover, with the (Day 2) baseline Halimeter score as the covariate.

Data was analyzed separately for each post-baseline measure. The other post-baseline scores (3-hour, 27-hour and Day 5) were analyzed for treatment differences using analysis of covariance methods as described above.

The Log 10 colony forming units (CFU) transformed estimates of organisms recovered on each of the three individual media were determined and reported for each subject at each of the three sampling time points (Baseline, 2-hour and Day 5) for each treatment period. The 2-hour micro sample on Day 1 and the Day 5 micro sample were assessed separately to determine treatment differences using similar ANCOVA methods discussed above using the Day 1 baseline sample as the covariate. In addition, the 2-hour reduction from baseline and the Day 5 reduction from baseline for each brush were tested versus zero using a paired t-test. Statistical tests for treatment effects were two-sided, carried out at the 5% significance level.

Results

Figure 8:
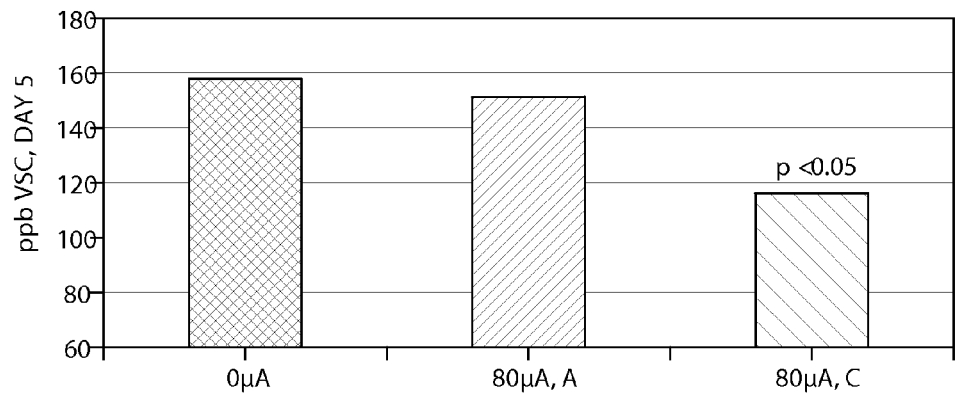
FIG. 8 is a chart that graphically depicts VSC Halimeter results on Day 5 of a study.

The VSC Halimeter results and the tongue sample GNA bacteria results on Day 5 of the study are shown in FIGS. 8 and 9, respectively. The vertical axis of the graph illustrated in FIG. 8 is the measured parts-per-billion (ppb) volatile sulfur compound content taken on Day 5. The vertical axis of the graph illustrated in FIG. 9 is the log GNA bacteria on the tongue, taken on Day 5. In both FIG. 8 and FIG. 9, the horizontal axis is labeled 0 μA for the non-ionic current treatment results, 80 μA, A for the anodic micro-current results, and 80 μA, C for the cathodic micro-current results.

As shown by FIG. 8, the anodic 80 μA micro-current provided a slight reduction in oral malodor, while the 80 μA micro-current provided a significant reduction in oral malodor compared with the zero micro-current treatment. Similarly, as shown in FIG. 9, the anodic 80 μA micro-current provided a GNA bacteria reduction over the zero micro-current treatment, and the cathodic 80 μA micro-current treatment provided a GNA bacteria reduction over the anodic 80 μA micro-current treatment.

Accordingly, it is shown that locally applied current may produce antibacterial benefits that translate into clinical efficacy.

Ramped Ionic Current Study

A study was performed to evaluate the effect of micro-currents of greater than 80 μA using a ramped micro-current control method on reduction of plaque and oral malodor. The study was a single-center, three treatment, randomized, three period, cross-over design. Up to twenty subjects were enrolled in the study. Generally, the study included an acclimation period of approximately 3 days prior to Period 1. Each of the three treatment periods of the cross-over study design were five days in duration (Monday through Friday). During each treatment period, subjects brushed their teeth under supervision at the testing site twice daily with their test products. They also brushed once daily at home (in the evening) with their acclimation products. Three DPIA images were captured each day (morning pre- and post-brushing and afternoon pre-brushing) except on the afternoon of Day 5 There was a minimum one week of wash out between treatment periods. The study procedures were repeated until the subjects completed three treatment periods using their randomly assigned treatment regimen.

Subjects having shown evidence of plaque (based on a screening procedure) were provided an acclimation kit box of acclimation products including two ADA reference manual toothbrushes and two tubes of Crest® Cavity Protection (4.6 oz) dentifrice (overtubed). The acclimation products were used: 1) during the acclimation period prior to Period 1; 2) as their evening brushing products during the treatment period; and 3) as washout products between each treatment period. For the acclimation/wash out period, subjects were instructed to use their acclimation products in place of their usual toothpaste and toothbrush for brushing (in their usual manner) twice a day. Subjects kept their acclimation products at home until their final Period 3, Day 5 visit.

Throughout the study, site staff reminded the subjects, either by phone or by e-mail, to perform the evening brushing by 11:00 pm the night before their Period 1 visit and to refrain from performing any oral hygiene the morning of the visit. In addition, the site staff reminded the subjects to abstain from eating, drinking, smoking, using breath mints, medicated lozenges (e.g., cough or throat drops), and chewing gum after completing the evening brushing. As with the studies described above, the subjects were informed that small sips of water were permissible, but they should refrain from drinking water 45 minutes prior to the visit.

The paste product for the study was a modified Crest Pro-Health tooth paste. As a modification the FDC blue component and all flavor components were left out of the dentifrice.

Day 1, Morning

Subjects returned to the site after refraining from all oral hygiene procedures the morning of their appointment time. A DPIA morning pre-brush image was taken.

For the DPIA measurement, subjects disclosed plaque (following a fluorescein plaque disclosing procedure, described above with respect to the Comparative Study) and have a pre-brush digital image taken (using UV imaging system as described above) of their anterior teeth.

Subjects were randomly assigned to a treatment sequence. Assignment to the treatment sequence took place on Period 1 only. The subjects used the same treatment product for the 5 day treatment period (Monday through Friday). The treatment products included a Panasonic® Twin Ionic EW-DE-40-01 brush handle (either no current, anodic current, or cathodic current, depending on the treatment sequence), and brush heads with conductive filaments. The filaments of the brush head were Nylon filaments having a conductive core (Nylon with carbon composites) and a non-conductive shell.

The applied current was zero current (treatment sequence A), a positive (anodic) square wave micro-current (treatment sequence B), or a negative (cathodic) square wave micro-current (treatment sequence C). The micro-current that was applied had a frequency of about 9 kHz and a duty cycle of about 80%. The micro-current amplitude was ramped as illustrated in FIG. 5C, with $I_{start}$ equal to 80 µA, $I_{step}$ 25 µA. The micro-current was incremented with a ramping speed of 80 µA/sec until a maximum micro-current amplitude ($I_{ramped}$) of about 400 µA was reached. Once 400 µA was reached, the micro-current amplitude stayed at this plateau until electrical contact was lost, as described above.

The subjects were provided with treatment brushing instructions (written and verbal) before use at treatment visits. The treatment brushing instructions were as follows:

Rinse mouth with tap water prior to brushing;
Securely attach brush head;
Grip the main body, with the hand touching the ion panel;
Wet brush head with tap water;
Apply the modified Crest Pro-Health tooth paste on the brush head
Wet hand that will hold brush;
Select a Mode (the first mode "powerful");
Place the brush head on the outside surface of upper teeth.
  The toothbrush bristles should be placed against the teeth at a slight angle towards the gum line;
Turn on toothbrush and start brushing in a slightly circular motion. Apply light pressure during brushing. After a few seconds, guide the bristles to the next section.
  Brush inside, outside and chewing surfaces of teeth with the same motion throughout;
Brush each quadrant for 30 seconds;
Finish brushing after two minutes;
Upon completion of brushing, turn the brush off by pressing the operation switch;
Rinse out residual paste by swishing 10 ml of water in mouth for 10 seconds; and
Expectorate in basin.

The subjects brushed with the treatment products by brushing their teeth as instructed twice a day (morning and afternoon supervised on site use). Following brushing, the subjects re-disclosed their plaque with fluorescein and a post brush morning DPIA image will be taken.

The subjects returned to the site for an afternoon visit. The subjects disclosed plaque and had a pre-brush afternoon DPIA image taken of their anterior teeth. Thereafter, the subjects brushed their teeth and their tongue with assigned toothbrush following morning instructions. The subjects brushed their teeth at home with acclimation products in the evening.

Days 2-4, Morning

The subjects returned to the site in the morning and disclosed their plaque (following the fluorescein plaque disclosing procedure) and had a pre-brush DPIA image taken of their anterior teeth. Thereafter, the subjects cleaned their teeth following the Day 1 instructions. Following brushing, the subjects re-disclosed their plaque with fluorescein and a post brush morning DPIA image was taken.

Days 2-4, Afternoon

The subjects returned to the site in the morning and disclosed their plaque (following the fluorescein plaque disclosing procedure) and had a pre-brush DPIA image taken of their anterior teeth. Thereafter, the subjects cleaned their teeth following the Day 1 instructions. Following brushing, the subjects re-disclosed their plaque with fluorescein and a post brush morning DPIA image was taken.

Day 5, Morning

The subjects returned to the site in the morning and disclosed their plaque (following the fluorescein plaque disclosing procedure) and had a pre-brush DPIA image taken of their anterior teeth. Thereafter, the subjects brushed their teeth and their tongue with the assigned treatment products following the above instructions. Following brushing, the subjects re-disclosed their plaque with fluorescein and a post brush morning DPIA image was taken.

The subjects were instructed to use their acclimation products over the following week (washout period) until their next treatment visit. They were reminded to refrain from all oral hygiene procedures the morning of their next appointment time; meaning their last brushing would be the evening (not later than 11 pm) prior to the scheduled visit day. In addition, subjects were reminded to abstain from eating, drinking, smoking, using breath mints, medicated lozenges (e.g., cough or throat drops), and chewing gum after completing the evening brushing. The subjects were informed that small sips of water would be permissible, but that they should refrain from drinking water 45 minutes prior to the visit.

Analysis

Morning Plaque Inhibition (Morning Pre-Brushing): For Days 2-5, the morning DPIA pre-brushing plaque coverage was analyzed separately for each day to determine treatment differences using an analysis of covariance (ANCOVA) for a crossover design with terms in the model for Subject (random effect), Period, Treatment, and if statistically significant at the 10% level, Carryover, with the Day 1 pre-brushing DPIA measurement as the covariate.

Afternoon Plaque Re-growth (Afternoon Pre-Brushing): For Days 1-4, the afternoon DPIA pre-brushing plaque coverage was analyzed separately for each day to determine treatment differences using an analysis of covariance (ANCOVA) for a crossover design with terms in the model for Subject (random effect), Period, Treatment, and if statistically significant at the 10% level, Carryover, with the Day 1 pre-brushing DPIA measurement as the covariate.

Plaque Reduction (Morning Pre-Brushing Minus Post-Brushing): For Days 1-5, the morning DPIA pre-brushing minus post-brushing (reduction) scores were analyzed separately by day to assess treatment effects using an analysis of covariance (ANCOVA) for a crossover design with terms in the model for Subject (random effect), Period, Treatment, and if statistically significant at the 10% level, Carryover, with the Day 1 pre-brushing DPIA measurement as the covariate.

Repeated Measures (Day Effects): Additionally, to look at the DPIA plaque trends across time, the following variables were analyzed separately using a repeated measures ANCOVA for a crossover design with terms in the model for Subject (random effect), Period, Treatment, Carryover (if significant) and Time with the Day 1 pre-brushing DPIA as the covariate:

Morning pre-brushing (Days 2-5),
Afternoon pre-brushing (Days 1-4), and
Plaque reductions (pre-minus post-brushing on Days 1-5).

Results

It should now be understood that embodiments described herein enable increased ionic micro-current levels in iontophoresis applications without imparting unpleasant sensations in the user or patient by ramping the micro-current from a start current to an end current over a rise time. In oral care applications, the ramped micro-current reduces the voltage drop in the oral cavity, and allows for current levels of greater than 100 µA. The ramping of micro-current techniques described herein may be implemented in any number of iontophoresis applications.

The dimensions and values disclosed herein are not to be understood as being strictly limited to the exact numerical values recited. Instead, unless otherwise specified, each such dimension is intended to mean both the recited value and a functionally equivalent range surrounding that value.

For example, a dimension disclosed as "40 mm" is intended to mean "about 40 mm" Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be understood to those skilled in the art that various other changes and modifications can be made without departing from the spirit and scope of the invention. It is therefore intended to cover in the appended claims all such changes and modifications that are within the scope of this invention.

What is claimed is:

1. A therapeutic micro-current delivery device comprising:
a first electrode operable to be in electrical contact with a user at a first user location;
a second electrode operable to be in electrical contact with the user at a second user location;
a power source operable to provide a first voltage potential at the first electrode and a second voltage potential at the second electrode;
a micro-current control circuit in electrical communication with the first electrode, the second electrode and the power source, wherein:
electrical contact of the first electrode at the first user location and electrical contact of the second electrode at the second user location completes an electrical circuit between the first electrode and the second electrode; and
upon a completion of the electrical circuit, the micro-current control circuit generates an alternating micro-current $I_{ramped}$ through a user between the first user location and the second user location that increases from a start current $I_{start}$ to an end current $I_{end}$ over a rise time $t_{rise}$, wherein $t_{rise}$ is between 1 second and 20 seconds; wherein $I_{end}$ is greater than 100 µA;
wherein the therapeutic micro-current delivery device is an oral care device.

2. The therapeutic micro-current delivery device of claim 1 wherein a maximum value of the end current $I_{end}$ is between 100 µA and 800 µA.

3. The therapeutic micro-current delivery device of claim 1 wherein a maximum value of the end current $I_{end}$ is between 400 µA and 800 µA.

4. The therapeutic micro-current delivery device of claim 1 wherein $t_{rise}$ is between 5 seconds and 20 seconds.

5. The therapeutic micro-current delivery device of claim 1 wherein $t_{rise}$ is between 15 seconds and 20 seconds.

6. The therapeutic micro-current delivery device of claim 1 wherein $t_{rise}$ is 16 seconds.

7. The therapeutic micro-current delivery device of claim 1 wherein:
the first user location is an oral cavity of the user; and
the micro-current $I_{ramped}$ generates a ramped current voltage drop $V_{ramped}$ that is less than a non-ramped current voltage drop $V_{non-ramped}$ that results from a non-ramped current $I_{non-ramped}$ upon a completion of the electrical circuit.

8. The therapeutic micro-current delivery device of claim 1 wherein the micro-current $I_{ramped}$ is an ionic current.

9. The therapeutic micro-current delivery device of claim 1 wherein the micro-current is increased between the start current $I_{start}$ to the end current $I_{end}$ as a continuous-time signal.

10. The therapeutic micro-current delivery device of claim 1 wherein the micro-current $I_{ramped}$ is increased stepwise from the start current $I_{start}$ to the end current $I_{end}$ over the rise time $t_{rise}$.

11. The therapeutic micro-current delivery device of claim 10 wherein the micro-current $I_{ramped}$ increases by a step current $I_{step}$ at a step frequency.

12. The therapeutic micro-current delivery device of claim 11 wherein the step frequency is variable.

13. The therapeutic micro-current delivery device of claim 1 wherein the end current $I_{end}$ is direct current.

14. The therapeutic micro-current delivery device of claim 1 wherein the micro-current $I_{ramped}$ comprises a duty cycle of 50%.

15. The therapeutic micro-current delivery device of claim 1 wherein the micro-current $I_{ramped}$ alternates between 0 and $(I_{start}+(m-1)I_{step})$ at an operational duty cycle, where m=1 upon a completion of the electrical circuit and increments by one at a step frequency until $(I_{start}+(m-1)I_{step})=I_{end}$ such that the micro-current $I_{ramped}$ alternates between 0 and $I_{end}$ after the rise time $t_{rise}$.

16. The therapeutic micro-current delivery device of claim 1 wherein the micro-current $I_{ramped}$ alternates between $(0+(m-1)I_{step})$ and $(I_{start}+(m-1)I_{step})$ at an operational duty cycle, where m=1 upon a completion of the electrical circuit and increments by one at a step frequency until $(I_{start}+(m-1)I_{step})=I_{end}$ such that the micro-current $I_{ramped}$ alternates between $(I_{end}-I_{start})$ and $I_{end}$ after the rise time $t_{rise}$.

17. The therapeutic micro-current delivery device of claim 1 wherein the micro-current $I_{ramped}$ alternates between $(-I_{start}-(m-1)I_{step})$ and $(I_{start}+(m-1)I_{step})$ at an operational duty cycle, where m=1 upon a completion of the electrical circuit and increments by one at a step frequency until $(I_{start}+(m-1)I_{step})=+I_{end}$ and $(-I_{start}-(m-1)I_{step})=-I_{end}$ such that the micro-current $I_{ramped}$ alternates between $-I_{end}$ and $+I_{end}$ after the rise time $t_{rise}$.

18. The therapeutic micro-current delivery device of claim 1 wherein the therapeutic micro-current delivery device is an electric toothbrush.

19. The therapeutic micro-current delivery device of claim 18 wherein the electric toothbrush comprises a vibrating actuator.

20. The therapeutic micro-current delivery device of claim 1 further comprising:
   a handle positioned on a first end of the therapeutic micro-current delivery device, wherein the second electrode is located on the handle; and
   an oral care implement positioned on a second end of the therapeutic micro-current delivery device, the oral care implement comprising brush filaments, wherein the first electrode is located proximate the brush filaments and the first user location is an oral cavity of the user.

21. The therapeutic micro-current delivery device of claim 20 wherein the brush filaments comprise conductive brush filaments that are electrically coupled to the first electrode.

22. The therapeutic micro-current delivery device of claim 20 wherein the first electrode comprises an insulated conductor wire, the insulated conductor wire comprising an electrically conductive wire core and an outer insulator jacket surrounding the electrically conductive wire core such that a portion of the electrically conductive wire core is exposed at an end of the insulated conductor wire.

23. An oral care device comprising:
   a handle portion;
   a brush head portion coupled to the handle portion, the brush head portion comprising brush filaments;
   a second electrode located in the handle portion and operable to be in electrical contact with a user at a first user location;
   a first electrode located in the brush head portion and operable to be in electrical contact with an oral cavity of the user at a second user location;
   a power source operable to provide a first voltage potential at the first electrode and a second voltage potential at the second electrode;
   a micro-current control circuit in electrical communication with the first electrode, the second electrode and the power source, wherein:
      electrical contact of the first electrode at the first user location and electrical contact of the second electrode at the second user location completes an electrical circuit between the first electrode and the second electrode;
      upon a completion of the electrical circuit, the micro-current control circuit generates an alternating micro-current $I_{ramped}$ through a user between the first user location and the second user location that increases from a start current $I_{start}$ to an end current $I_{end}$ over a rise time $t_{rise}$, wherein $t_{rise}$ is 16 seconds;
   wherein $I_{start}$ is 80 µA;
   wherein $I_{end}$ is between 400 µA and 800 µA;
   wherein the alternating micro-current $I_{ramped}$ increases by a step current $I_{step}$ at a step frequency and wherein $I_{step}$ is 80 µA.

* * * * *